(12) United States Patent
Hazeki et al.

(10) Patent No.: US 8,329,420 B2
(45) Date of Patent: Dec. 11, 2012

(54) SCREENING METHOD FOR A SUBSTANCE THAT BINDS TO AN INTRACELLULAR REGION OF TLR4

(75) Inventors: Osamu Hazeki, Hiroshima (JP); Kaoru Hazeki, Hiroshima (JP); Masayuki Ii, Osaka (JP); Naoko Matsunaga, Osaka (JP)

(73) Assignees: Hiroshima University, Hiroshima (JP); Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/225,721

(22) PCT Filed: Mar. 29, 2007

(86) PCT No.: PCT/JP2007/056962
§ 371 (c)(1),
(2), (4) Date: Mar. 6, 2009

(87) PCT Pub. No.: WO2007/114296
PCT Pub. Date: Oct. 11, 2007

(65) Prior Publication Data
US 2009/0317833 A1 Dec. 24, 2009

(30) Foreign Application Priority Data

Mar. 30, 2006 (JP) ................. 2006-095936

(51) Int. Cl.
| | |
|---|---|
| G01N 33/567 | (2006.01) |
| C12N 1/21 | (2006.01) |
| C12N 1/19 | (2006.01) |
| C12N 5/10 | (2006.01) |
| C12N 5/16 | (2006.01) |
| C12N 5/18 | (2006.01) |
| C12N 5/22 | (2006.01) |
| C07K 14/705 | (2006.01) |

(52) U.S. Cl. ................. 435/7.21; 435/252.3; 435/254.2; 435/348; 435/352; 435/365; 435/366; 435/369; 530/350

(58) Field of Classification Search .................. None
See application file for complete search history.

(56) References Cited

FOREIGN PATENT DOCUMENTS
| | | |
|---|---|---|
| EP | 1 495 756 A1 | 1/2005 |
| JP | 2004-002370 A | 1/2004 |
| WO | WO 03/084527 A1 | 10/2003 |
| WO | WO 2004/053452 A2 | 6/2004 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Arroyo-Espliguero et al., "CD14 and toll-like receptor 4: a link between infection and acute coronary events?", 90:983-988, Heart, 2004.
Akira et al., "Pathogen Recognition and Innate Immunity," Cell, Feb. 24, 2006, 124:783-801.
Ii et al., "A Novel Cyclohexene Derivative, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production through Suppression of Intracellular Signaling," Molecular Pharmacology, 2006, 69(4):1288-1295.
Verstak et al., "Toll-like receptor signaling and the clinical benefits that lie within," Inflamm. Res., 2007, 56:1-10.
Supplementary European Search Report dated Oct. 8, 2009, in corresponding EP 07740400.2, 4 pages.
Miyake, Kensuke, "Endotoxin Recognition Molecules MD-2 and Toll-like Receptor 4 as Potential Targets for Therapeutic Intervention of Endotoxin Shock," Current Drug Targets—Inflammation & Allergy, 2004, 3(3):291-297.
Takashima et al., "Analysis of binding site for the novel small-molecule TLR4 signal transduction inhibitor TAK-242 and its therapeutic effect on mouse sepsis model," British Journal of Pharmacology, 2009, 157:1250-1262.
Yamada et al., "Discovery of Novel and Potent Small-Molecule Inhibitors of NO and Cytokine Production as Antisepsis Agents: Synthesis and Biological Activity of Alkyl 6-(N-Substituted sulfamoyl)cyclohex-1-ene-1-carboxylate," J. Med. Chem., 2005, 48(23):7457-7467.

* cited by examiner

Primary Examiner — Zachary Howard
(74) Attorney, Agent, or Firm — Foley & Lardner LLP

(57) ABSTRACT

The present invention provides a method of screening for a drug for the prophylaxis or treatment of at least one disease selected from the group consisting of cardiac disease, autoimmune disease, inflammatory disease, central nervous system disease, infectious disease, sepsis, severe sepsis and septic shock, which includes selecting a substance that binds to an intracellular region of TLR4, and inhibits signal transduction from said molecule, and a kit for this method, which contains (1) a cell that expresses wild-type TLR4 and (2) a cell that expresses a mutant TLR4, and which can detect a signal from TLR4 with expression of a reporter gene as an index.

2 Claims, 6 Drawing Sheets

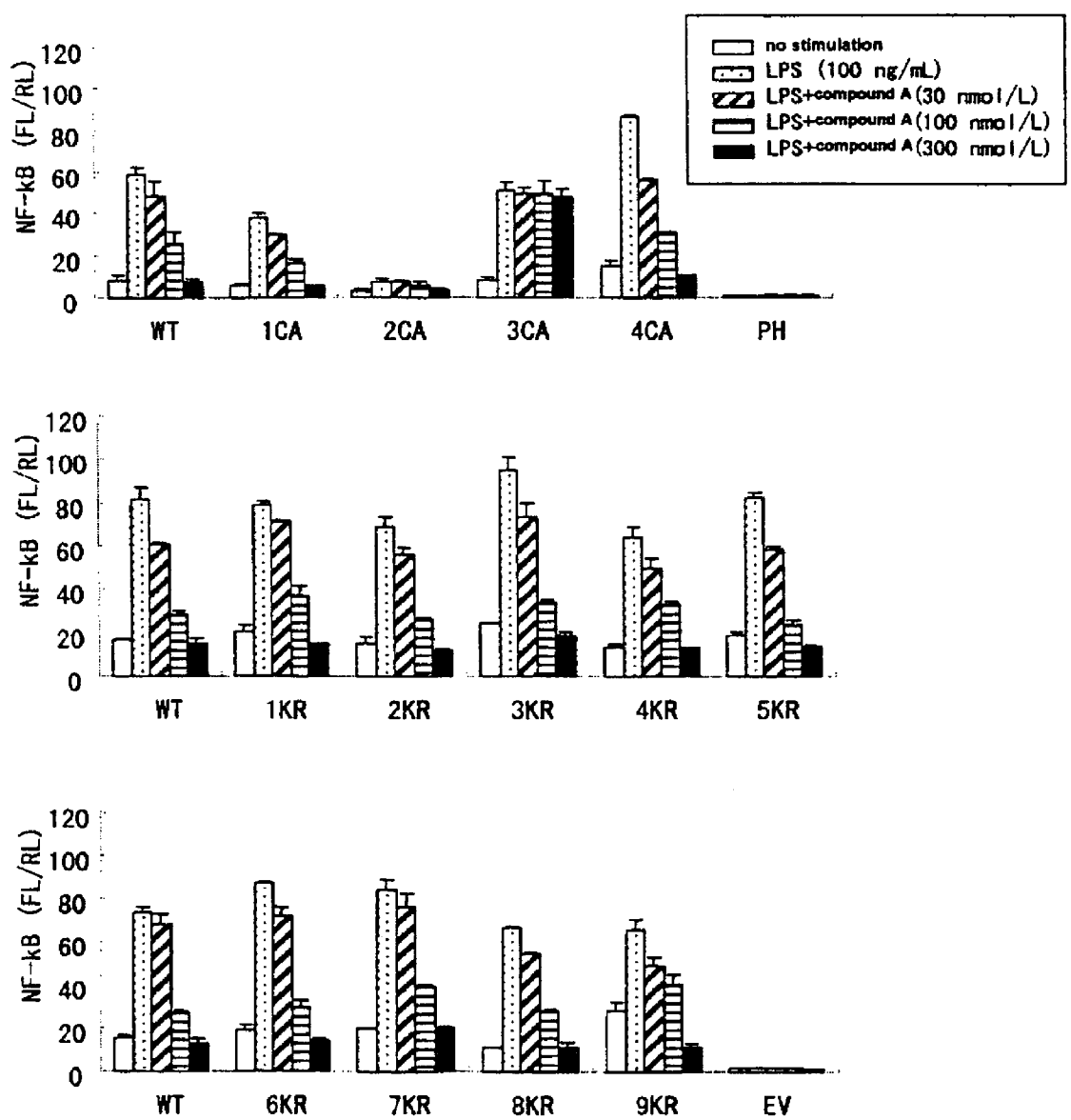
FIG. 3-A

FIG. 3-B
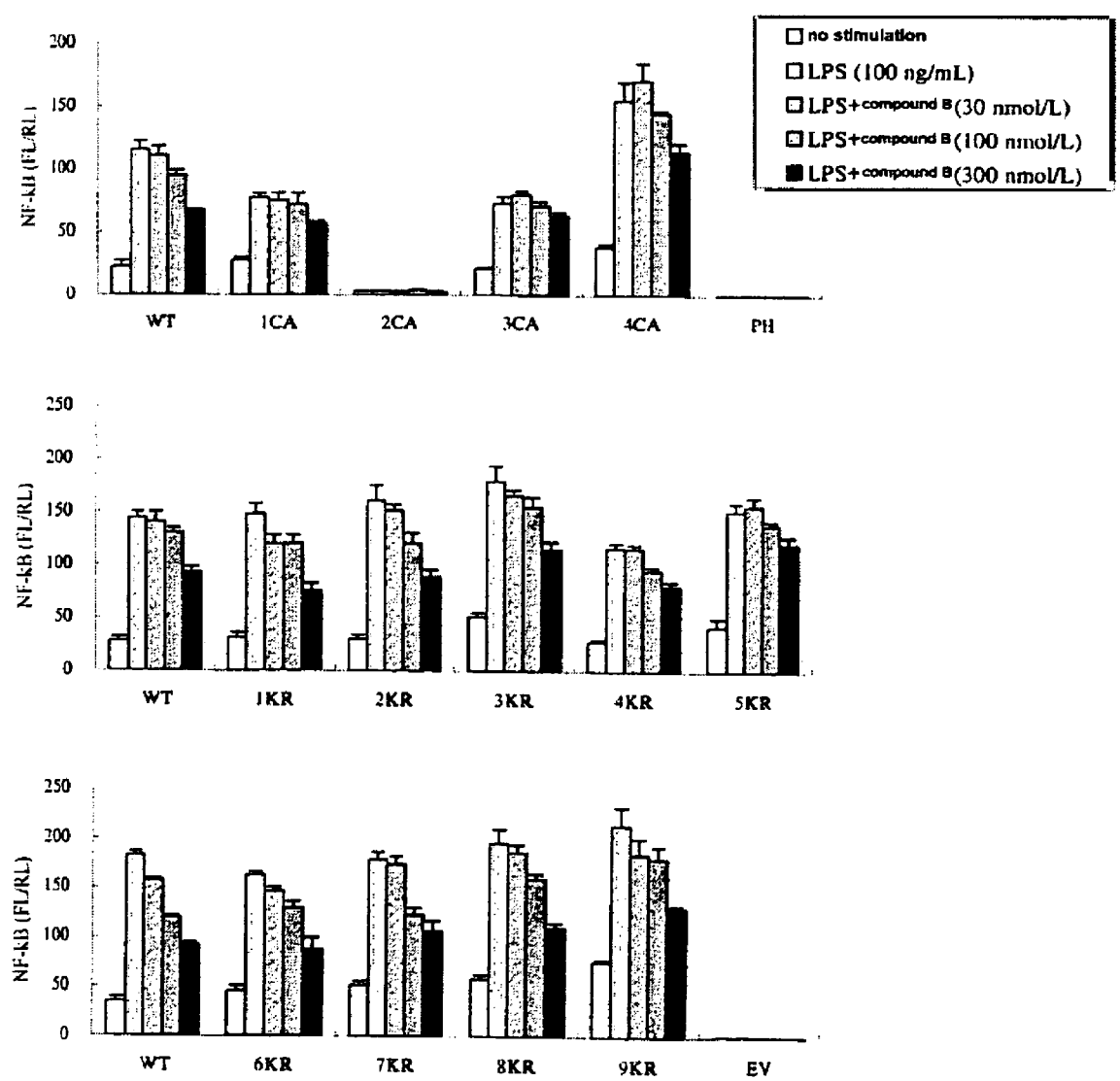

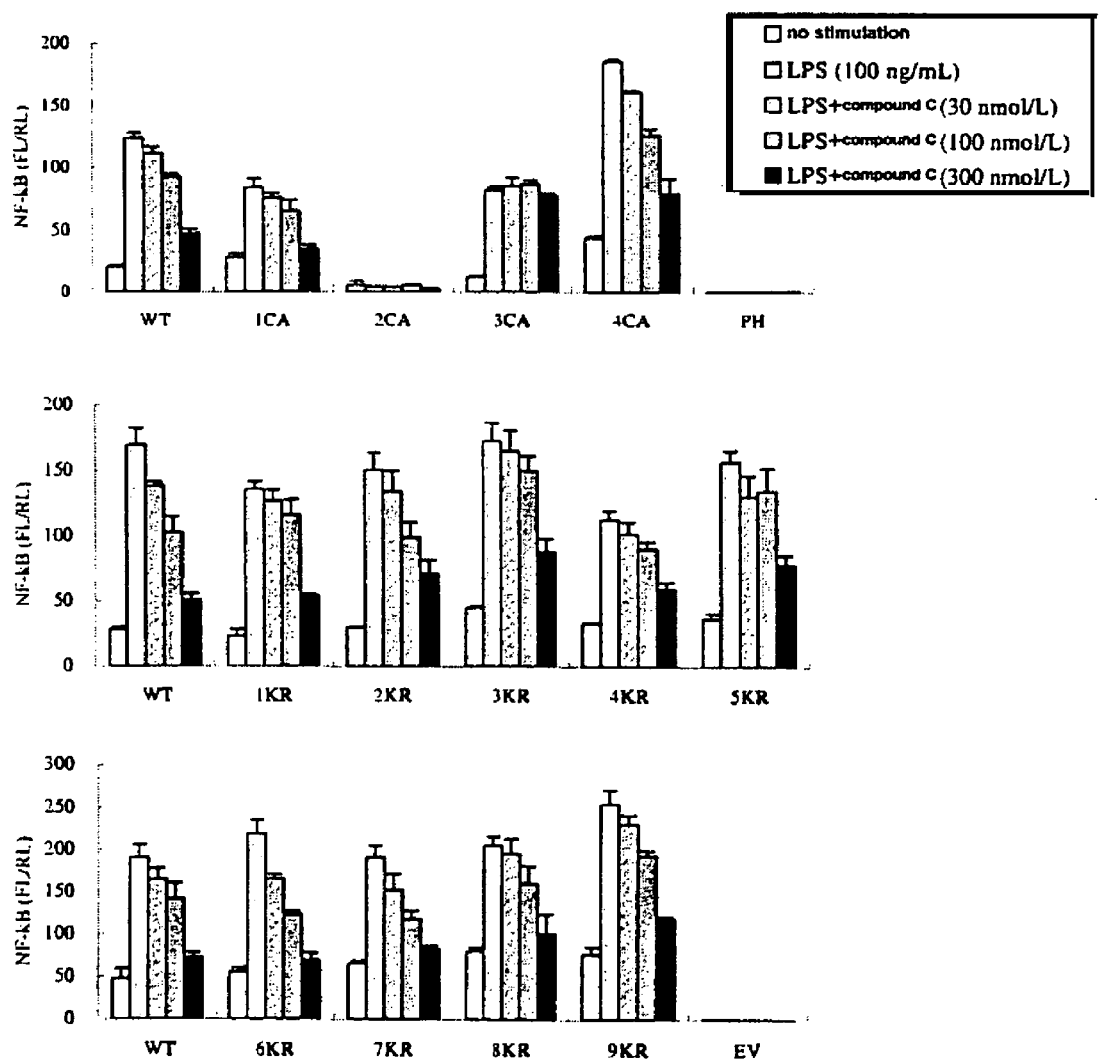
FIG. 3-C

FIG. 3-D
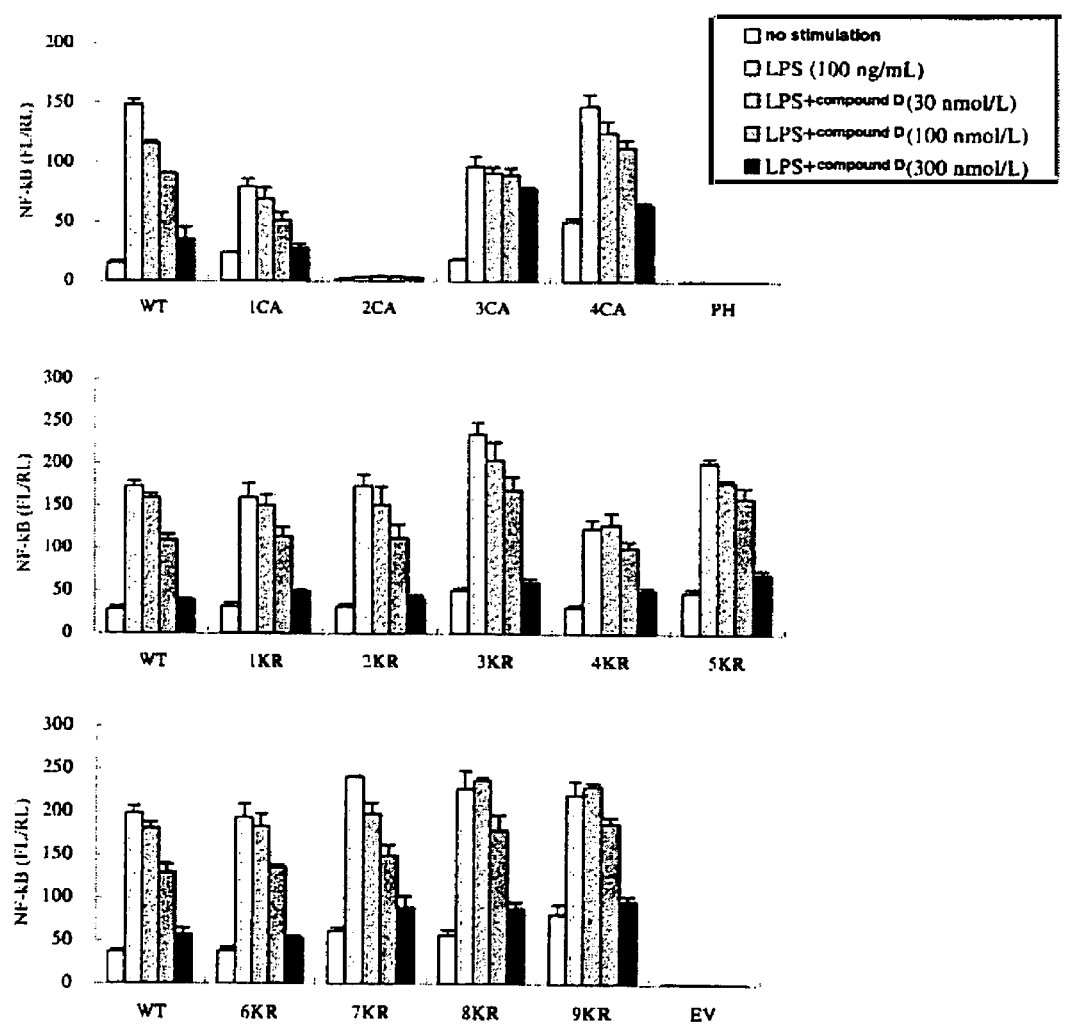

SEQUENCE LISTING

```
<160> NUMBER OF SEQ ID NOS: 38

<210> SEQ ID NO 1
<211> LENGTH: 2517
<212> TYPE: DNA
<213> ORGANISM: Homo sapiens
<220> FEATURE:
<221> NAME/KEY: CDS
<222> LOCATION: (1)..(2517)

<400> SEQUENCE: 1 atg atg tct gcc tcg cgc ctg gct ggg act ctg atc cca gcc atg gcc        48
Met Met Ser Ala Ser Arg Leu Ala Gly Thr Leu Ile Pro Ala Met Ala
1               5                   10                  15 ttc ctc tcc tgc gtg aga cca gaa agc tgg gag ccc tgc gtg gag gtg        96
Phe Leu Ser Cys Val Arg Pro Glu Ser Trp Glu Pro Cys Val Glu Val
                20                  25                  30 gtt cct aat att act tat caa tgc atg gag ctg aat ttc tac aaa atc       144
Val Pro Asn Ile Thr Tyr Gln Cys Met Glu Leu Asn Phe Tyr Lys Ile
            35                  40                  45 ccc gac aac ctc ccc ttc tca acc aag aac ctg gac ctg agc ttt aat       192
Pro Asp Asn Leu Pro Phe Ser Thr Lys Asn Leu Asp Leu Ser Phe Asn
        50                  55                  60 ccc ctg agg cat tta ggc agc tat agc ttc ttc agt ttc cca gaa ctg       240
Pro Leu Arg His Leu Gly Ser Tyr Ser Phe Phe Ser Phe Pro Glu Leu
    65                  70                  75                  80 cag gtg ctg gat tta tcc agg tgt gaa atc cag aca att gaa gat ggg       288
Gln Val Leu Asp Leu Ser Arg Cys Glu Ile Gln Thr Ile Glu Asp Gly
                85                  90                  95 gca tat cag agc cta agc cac ctc tct acc tta ata ttg aca gga aac       336
Ala Tyr Gln Ser Leu Ser His Leu Ser Thr Leu Ile Leu Thr Gly Asn
                100                 105                 110 ccc atc cag agt tta gcc ctg gga gcc ttt tct gga cta tca agt tta       384
Pro Ile Gln Ser Leu Ala Leu Gly Ala Phe Ser Gly Leu Ser Ser Leu
```

```
                   115                 120                 125
cag aag ctg gtg gct gtg gag aca aat cta gca tct cta gag aac ttc        432
Gln Lys Leu Val Ala Val Glu Thr Asn Leu Ala Ser Leu Glu Asn Phe
    130                 135                 140 ccc att gga cat ctc aaa act ttg aaa gaa ctt aat gtg gct cac aat        480
Pro Ile Gly His Leu Lys Thr Leu Lys Glu Leu Asn Val Ala His Asn
145                 150                 155                 160 ctt atc caa tct ttc aaa tta cct gag tat ttt tct aat ctg acc aat        528
Leu Ile Gln Ser Phe Lys Leu Pro Glu Tyr Phe Ser Asn Leu Thr Asn
                165                 170                 175 cta gag cac ttg gac ctt tcc agc aac aag att caa agt att tat tgc        576
Leu Glu His Leu Asp Leu Ser Ser Asn Lys Ile Gln Ser Ile Tyr Cys
            180                 185                 190 aca gac ttg cgg gtt cta cat caa atg ccc cta ctc aat ctc tct tta        624
Thr Asp Leu Arg Val Leu His Gln Met Pro Leu Leu Asn Leu Ser Leu
        195                 200                 205 gac ctg tcc ctg aac cct atg aac ttt atc caa cca ggt gca ttt aaa        672
Asp Leu Ser Leu Asn Pro Met Asn Phe Ile Gln Pro Gly Ala Phe Lys
    210                 215                 220 gaa att agg ctt cat aag ctg act tta aga aat aat ttt gat agt tta        720
Glu Ile Arg Leu His Lys Leu Thr Leu Arg Asn Asn Phe Asp Ser Leu
225                 230                 235                 240 aat gta atg aaa act tgt att caa ggt ctg gct ggt tta gaa gtc cat        768
Asn Val Met Lys Thr Cys Ile Gln Gly Leu Ala Gly Leu Glu Val His
                245                 250                 255 cgt ttg gtt ctg gga gaa ttt aga aat gaa gga aac ttg gaa aag ttt        816
Arg Leu Val Leu Gly Glu Phe Arg Asn Glu Gly Asn Leu Glu Lys Phe
            260                 265                 270 gac aaa tct gct cta gag ggc ctg tgc aat ttg acc att gaa gaa ttc        864
Asp Lys Ser Ala Leu Glu Gly Leu Cys Asn Leu Thr Ile Glu Glu Phe
        275                 280                 285 cga tta gca tac tta gac tac tac ctc gat gat att att gac tta ttt        912
Arg Leu Ala Tyr Leu Asp Tyr Tyr Leu Asp Asp Ile Ile Asp Leu Phe
    290                 295                 300 aat tgt ttg aca aat gtt tct tca ttt tcc ctg gtg agt gtg act att        960
Asn Cys Leu Thr Asn Val Ser Ser Phe Ser Leu Val Ser Val Thr Ile
305                 310                 315                 320 gaa agg gta aaa gac ttt tct tat aat ttc gga tgg caa cat tta gaa       1008
Glu Arg Val Lys Asp Phe Ser Tyr Asn Phe Gly Trp Gln His Leu Glu
                325                 330                 335 tta gtt aac tgt aaa ttt gga cag ttt ccc aca ttg aaa ctc aaa tct       1056
Leu Val Asn Cys Lys Phe Gly Gln Phe Pro Thr Leu Lys Leu Lys Ser
            340                 345                 350 ctc aaa agg ctt act ttc act tcc aac aaa ggt ggg aat gct ttt tca       1104
Leu Lys Arg Leu Thr Phe Thr Ser Asn Lys Gly Gly Asn Ala Phe Ser
        355                 360                 365 gaa gtt gat cta cca agc ctt gag ttt cta gat ctc agt aga aat ggc       1152
Glu Val Asp Leu Pro Ser Leu Glu Phe Leu Asp Leu Ser Arg Asn Gly
    370                 375                 380 ttg agt ttc aaa ggt tgc tgt tct caa agt gat ttt ggg aca acc agc       1200
Leu Ser Phe Lys Gly Cys Cys Ser Gln Ser Asp Phe Gly Thr Thr Ser
385                 390                 395                 400 cta aag tat tta gat ctg agc ttc aat ggt gtt att acc atg agt tca       1248
Leu Lys Tyr Leu Asp Leu Ser Phe Asn Gly Val Ile Thr Met Ser Ser
                405                 410                 415 aac ttc ttg ggc tta gaa caa cta gaa cat ctg gat ttc cag cat tcc       1296
Asn Phe Leu Gly Leu Glu Gln Leu Glu His Leu Asp Phe Gln His Ser
            420                 425                 430 aat ttg aaa caa atg agt gag ttt tca gta ttc cta tca ctc aga aac       1344
Asn Leu Lys Gln Met Ser Glu Phe Ser Val Phe Leu Ser Leu Arg Asn
```

-continued

| | | | | |
|---|---|---|---|---|
| | 435 | 440 | 445 | |
| ctc att tac ctt gac att tct cat act cac acc aga gtt gct ttc aat<br>Leu Ile Tyr Leu Asp Ile Ser His Thr His Thr Arg Val Ala Phe Asn<br>450 455 460 | | | | 1392 |
| ggc atc ttc aat ggc ttg tcc agt ctc gaa gtc ttg aaa atg gct ggc<br>Gly Ile Phe Asn Gly Leu Ser Ser Leu Glu Val Leu Lys Met Ala Gly<br>465 470 475 480 | | | | 1440 |
| aat tct ttc cag gaa aac ttc ctt cca gat atc ttc aca gag ctg aga<br>Asn Ser Phe Gln Glu Asn Phe Leu Pro Asp Ile Phe Thr Glu Leu Arg<br>485 490 495 | | | | 1488 |
| aac ttg acc ttc ctg gac ctc tct cag tgt caa ctg gag cag ttg tct<br>Asn Leu Thr Phe Leu Asp Leu Ser Gln Cys Gln Leu Glu Gln Leu Ser<br>500 505 510 | | | | 1536 |
| cca aca gca ttt aac tca ctc tcc agt ctt cag gta cta aat atg agc<br>Pro Thr Ala Phe Asn Ser Leu Ser Ser Leu Gln Val Leu Asn Met Ser<br>515 520 525 | | | | 1584 |
| cac aac aac ttc ttt tca ttg gat acg ttt cct tat aag tgt ctg aac<br>His Asn Asn Phe Phe Ser Leu Asp Thr Phe Pro Tyr Lys Cys Leu Asn<br>530 535 540 | | | | 1632 |
| tcc ctc cag gtt ctt gat tac agt ctc aat cac ata atg act tcc aaa<br>Ser Leu Gln Val Leu Asp Tyr Ser Leu Asn His Ile Met Thr Ser Lys<br>545 550 555 560 | | | | 1680 |
| aaa cag gaa cta cag cat ttt cca agt agt cta gct ttc tta aat ctt<br>Lys Gln Glu Leu Gln His Phe Pro Ser Ser Leu Ala Phe Leu Asn Leu<br>565 570 575 | | | | 1728 |
| act cag aat gac ttt gct tgt act tgt gaa cac cag agt ttc ctg caa<br>Thr Gln Asn Asp Phe Ala Cys Thr Cys Glu His Gln Ser Phe Leu Gln<br>580 585 590 | | | | 1776 |
| tgg atc aag gac cag agg cag ctc ttg gtg gaa gtt gaa cga atg gaa<br>Trp Ile Lys Asp Gln Arg Gln Leu Leu Val Glu Val Glu Arg Met Glu<br>595 600 605 | | | | 1824 |
| tgt gca aca cct tca gat aag cag ggc atg cct gtg ctg agt ttg aat<br>Cys Ala Thr Pro Ser Asp Lys Gln Gly Met Pro Val Leu Ser Leu Asn<br>610 615 620 | | | | 1872 |
| atc acc tgt cag atg aat aag acc atc att ggt gtg tcg gtc ctc agt<br>Ile Thr Cys Gln Met Asn Lys Thr Ile Ile Gly Val Ser Val Leu Ser<br>625 630 635 640 | | | | 1920 |
| gtg ctt gta gta tct gtt gta gca gtt ctg gtc tat aag ttc tat ttt<br>Val Leu Val Val Ser Val Val Ala Val Leu Val Tyr Lys Phe Tyr Phe<br>645 650 655 | | | | 1968 |
| cac ctg atg ctt ctt gct ggc tgc ata aag tat ggt aga ggt gaa aac<br>His Leu Met Leu Leu Ala Gly Cys Ile Lys Tyr Gly Arg Gly Glu Asn<br>660 665 670 | | | | 2016 |
| atc tat gat gcc ttt gtt atc tac tca agc cag gat gag gac tgg gta<br>Ile Tyr Asp Ala Phe Val Ile Tyr Ser Ser Gln Asp Glu Asp Trp Val<br>675 680 685 | | | | 2064 |
| agg aat gag cta gta aag aat tta gaa gaa ggg gtg cct cca ttt cag<br>Arg Asn Glu Leu Val Lys Asn Leu Glu Glu Gly Val Pro Pro Phe Gln<br>690 695 700 | | | | 2112 |
| ctc tgc ctt cac tac aga gac ttt att ccc ggt gtg gcc att gct gcc<br>Leu Cys Leu His Tyr Arg Asp Phe Ile Pro Gly Val Ala Ile Ala Ala<br>705 710 715 720 | | | | 2160 |
| aac atc atc cat gaa ggt ttc cat aaa agc cga aag gtg att gtt gtg<br>Asn Ile Ile His Glu Gly Phe His Lys Ser Arg Lys Val Ile Val Val<br>725 730 735 | | | | 2208 |
| gtg tcc cag cac ttc atc cag agc cgc tgg tgt atc ttt gaa tat gag<br>Val Ser Gln His Phe Ile Gln Ser Arg Trp Cys Ile Phe Glu Tyr Glu<br>740 745 750 | | | | 2256 |
| att gct cag acc tgg cag ttt ctg agc agt cgt gct ggt atc atc ttc<br>Ile Ala Gln Thr Trp Gln Phe Leu Ser Ser Arg Ala Gly Ile Ile Phe | | | | 2304 |

```
                    755                 760                 765
att gtc ctg cag aag gtg gag aag acc ctg ctc agg cag cag gtg gag    2352
Ile Val Leu Gln Lys Val Glu Lys Thr Leu Leu Arg Gln Gln Val Glu
770                 775                 780 ctg tac cgc ctt ctc agc agg aac act tac ctg gag tgg gag gac agt    2400
Leu Tyr Arg Leu Leu Ser Arg Asn Thr Tyr Leu Glu Trp Glu Asp Ser
785                 790                 795                 800 gtc ctg ggg cgg cac atc ttc tgg aga cga ctc aga aaa gcc ctg ctg    2448
Val Leu Gly Arg His Ile Phe Trp Arg Arg Leu Arg Lys Ala Leu Leu
            805                 810                 815 gat ggt aaa tca tgg aat cca gaa gga aca gtg ggt aca gga tgc aat    2496
Asp Gly Lys Ser Trp Asn Pro Glu Gly Thr Val Gly Thr Gly Cys Asn
        820                 825                 830 tgg cag gaa gca aca tct atc                                        2517
Trp Gln Glu Ala Thr Ser Ile
        835

<210> SEQ ID NO 2
<211> LENGTH: 839
<212> TYPE: PRT
<213> ORGANISM: Homo sapiens

<400> SEQUENCE: 2

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
        35                  40                  45

Pro Asp Asn Leu Pro Phe Ser Thr Lys Asn Leu Asp Leu Ser Phe Asn
    50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270
```

```
Asp Lys Ser Ala Leu Glu Gly Leu Cys Asn Leu Thr Ile Glu Glu Phe
        275                 280                 285
Arg Leu Ala Tyr Leu Asp Tyr Tyr Leu Asp Asp Ile Ile Asp Leu Phe
        290                 295                 300
Asn Cys Leu Thr Asn Val Ser Ser Phe Ser Leu Val Ser Val Thr Ile
305                 310                 315                 320
Glu Arg Val Lys Asp Phe Ser Tyr Asn Phe Gly Trp Gln His Leu Glu
                325                 330                 335
Leu Val Asn Cys Lys Phe Gly Gln Phe Pro Thr Leu Lys Leu Lys Ser
                340                 345                 350
Leu Lys Arg Leu Thr Phe Thr Ser Asn Lys Gly Gly Asn Ala Phe Ser
        355                 360                 365
Glu Val Asp Leu Pro Ser Leu Glu Phe Leu Asp Leu Ser Arg Asn Gly
        370                 375                 380
Leu Ser Phe Lys Gly Cys Cys Ser Gln Ser Asp Phe Gly Thr Thr Ser
385                 390                 395                 400
Leu Lys Tyr Leu Asp Leu Ser Phe Asn Gly Val Ile Thr Met Ser Ser
                405                 410                 415
Asn Phe Leu Gly Leu Glu Gln Leu Glu His Leu Asp Phe Gln His Ser
        420                 425                 430
Asn Leu Lys Gln Met Ser Glu Phe Ser Val Phe Leu Ser Leu Arg Asn
        435                 440                 445
Leu Ile Tyr Leu Asp Ile Ser His Thr His Thr Arg Val Ala Phe Asn
450                 455                 460
Gly Ile Phe Asn Gly Leu Ser Ser Leu Glu Val Leu Lys Met Ala Gly
465                 470                 475                 480
Asn Ser Phe Gln Glu Asn Phe Leu Pro Asp Ile Phe Thr Glu Leu Arg
                485                 490                 495
Asn Leu Thr Phe Leu Asp Leu Ser Gln Cys Gln Leu Glu Gln Leu Ser
                500                 505                 510
Pro Thr Ala Phe Asn Ser Leu Ser Ser Leu Gln Val Leu Asn Met Ser
        515                 520                 525
His Asn Asn Phe Phe Ser Leu Asp Thr Phe Pro Tyr Lys Cys Leu Asn
        530                 535                 540
Ser Leu Gln Val Leu Asp Tyr Ser Leu Asn His Ile Met Thr Ser Lys
545                 550                 555                 560
Lys Gln Glu Leu Gln His Phe Pro Ser Ser Leu Ala Phe Leu Asn Leu
                565                 570                 575
Thr Gln Asn Asp Phe Ala Cys Thr Cys Glu His Gln Ser Phe Leu Gln
                580                 585                 590
Trp Ile Lys Asp Gln Arg Gln Leu Leu Val Glu Val Glu Arg Met Glu
        595                 600                 605
Cys Ala Thr Pro Ser Asp Lys Gln Gly Met Pro Val Leu Ser Leu Asn
        610                 615                 620
Ile Thr Cys Gln Met Asn Lys Thr Ile Ile Gly Val Ser Val Leu Ser
625                 630                 635                 640
Val Leu Val Val Ser Val Val Ala Val Leu Val Tyr Lys Phe Tyr Phe
                645                 650                 655
His Leu Met Leu Leu Ala Gly Cys Ile Lys Tyr Gly Arg Gly Glu Asn
                660                 665                 670
Ile Tyr Asp Ala Phe Val Ile Tyr Ser Ser Gln Asp Glu Asp Trp Val
        675                 680                 685
Arg Asn Glu Leu Val Lys Asn Leu Glu Glu Gly Val Pro Pro Phe Gln
```

```
                690             695             700
Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835
```

```
<210> SEQ ID NO 3
<211> LENGTH: 10
<212> TYPE: DNA
<213> ORGANISM: Homo sapiens
<220> FEATURE:
<221> NAME/KEY: misc_feature
<222> LOCATION: (5)..(6)
<223> OTHER INFORMATION: n is a, c, g, or t

<400> SEQUENCE: 3 gggrnnyycc                                                              10

<210> SEQ ID NO 4
<211> LENGTH: 12
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is a, c, g, or t

<400> SEQUENCE: 4
gaaassgaaa ny                                                           12

<210> SEQ ID NO 5
<211> LENGTH: 30
<212> TYPE: DNA
<213> ORGANISM: Artificial
<220> FEATURE:
<223> OTHER INFORMATION: Oligonucleotide designed to act as primer for
      amplifying TIRAP cDNA.

<400> SEQUENCE: 5
gcgcggatcc atggcatcat cgacctccct                                        30

<210> SEQ ID NO 6
<211> LENGTH: 29
<212> TYPE: DNA
<213> ORGANISM: Artificial
<220> FEATURE:
<223> OTHER INFORMATION: Oligonucleotide designed to act as primer for
      amplifying TIRAP cDNA.

<400> SEQUENCE: 6
```

```
gcgcgcggcc gctcaaagta gatcagata                                    29
```

<210> SEQ ID NO 7
<211> LENGTH: 30
<212> TYPE: DNA
<213> ORGANISM: Artificial
<220> FEATURE:
<223> OTHER INFORMATION: Oligonucleotide designed to act as primer for
      amplifying TIR domain of TLR2 gene.

<400> SEQUENCE: 7

```
ggatcctatg atgcatttgt ttcttacagt                                   30
```

<210> SEQ ID NO 8
<211> LENGTH: 34
<212> TYPE: DNA
<213> ORGANISM: Artificial
<220> FEATURE:
<223> OTHER INFORMATION: Oligonucleotide designed to act as primer for
      amplifying TIR domain of TLR2 gene.

<400> SEQUENCE: 8

```
aagcggccgc ctaggacttt atcgcagctc tcag                              34
```

<210> SEQ ID NO 9
<211> LENGTH: 30
<212> TYPE: DNA
<213> ORGANISM: Artificial
<220> FEATURE:
<223> OTHER INFORMATION: Oligonucleotide designed to act as primer for
      amplifying TIR domain of TLR4 gene.

<400> SEQUENCE: 9

```
ggatcctatg atgcctttgt tatctactca                                   30
```

<210> SEQ ID NO 10
<211> LENGTH: 34
<212> TYPE: DNA
<213> ORGANISM: Artificial
<220> FEATURE:
<223> OTHER INFORMATION: Oligonucleotide designed to act as primer for
      amplifying TIR domain of TLR4 gene.

<400> SEQUENCE: 10

```
aagcggccgc tcagatagat gttgcttcct gcca                              34
```

<210> SEQ ID NO 11
<211> LENGTH: 36
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 11

```
tgatgcttct tgctggcgcc ataaagtatg gtagag                            36
```

<210> SEQ ID NO 12
<211> LENGTH: 36
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 12

```
ctctaccata ctttatggcg ccagcaagaa gcatca                            36
```

<210> SEQ ID NO 13
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 13
cctccatttc agctcgccct tcactacaga ga                                   32

<210> SEQ ID NO 14
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 14
tctctgtagt gaagggcgag ctgaaatgga gg                                   32

<210> SEQ ID NO 15
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 15
atccagagcc gctgggctat ctttgaatat ga                                   32

<210> SEQ ID NO 16
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 16
tcatattcaa agatagccca gcggctctgg at                                   32

<210> SEQ ID NO 17
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 17
acagtgggta caggagccaa ttggcaggaa gc                                   32

<210> SEQ ID NO 18
<211> LENGTH: 32
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 18
gcttcctgcc aattggctcc tgtacccact gt                                   32

<210> SEQ ID NO 19
<211> LENGTH: 32
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 19
tacagagact ttattcacgg tgtggccatt gc                                 32

<210> SEQ ID NO 20
<211> LENGTH: 32
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 20
gcaatggcca caccgtgaat aaagtctctg ta                                 32

<210> SEQ ID NO 21
<211> LENGTH: 32
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 21
cagttctggt ctataggttc tattttcacc tg                                 32

<210> SEQ ID NO 22
<211> LENGTH: 32
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 22
caggtgaaaa tagaacctat agaccagaac tg                                 32

<210> SEQ ID NO 23
<211> LENGTH: 29
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 23
tgctggctgc ataaggtatg gtagaggtg                                     29

<210> SEQ ID NO 24
<211> LENGTH: 29
<212> TYPE: DNA
<213> ORGANISM: Artificial
<220> FEATURE:
<223> OTHER INFORMATION: Oligonucletide designed to act as primer for amplifying mutant TLR4 cDNA.

<400> SEQUENCE: 24
cacctctacc ataccttatg cagccagca                                     29

<210> SEQ ID NO 25
<211> LENGTH: 31

```
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 25
ggaatgagct agtaaggaat ttagaagaag g                                      31

<210> SEQ ID NO 26
<211> LENGTH: 31
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 26
ccttcttcta aattccttac tagctcattc c                                      31

<210> SEQ ID NO 27
<211> LENGTH: 33
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 27
catgaaggtt tccatagaag ccgaaaggtg att                                    33

<210> SEQ ID NO 28
<211> LENGTH: 33
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 28
aatcaccttt cggcttctat ggaaaccttc atg                                    33

<210> SEQ ID NO 29
<211> LENGTH: 29
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 29
ccataaaagc cgaagggtga ttgttgtgg                                         29

<210> SEQ ID NO 30
<211> LENGTH: 29
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 30
ccacaacaat caccctccgg cttttatgg                                         29

<210> SEQ ID NO 31
<211> LENGTH: 28
<212> TYPE: DNA
<213> ORGANISM: Artificial
```

```
<220> FEATURE:
<223> OTHER INFORMATION: Oligonucletide designed to act as primer for
      amplifying mutant TLR4 cDNA.

<400> SEQUENCE: 31
cattgtcctg cagagggtgg agaagacc                                            28

<210> SEQ ID NO 32
<211> LENGTH: 28
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 32
ggtcttctcc accctctgca ggacaatg                                            28

<210> SEQ ID NO 33
<211> LENGTH: 28
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 33
cagaaggtgg agaggaccct gctcaggc                                            28

<210> SEQ ID NO 34
<211> LENGTH: 28
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 34
gcctgagcag ggtcctctcc accttctg                                            28

<210> SEQ ID NO 35
<211> LENGTH: 29
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 35
gagacgactc agaagagccc tgctggatg                                           29

<210> SEQ ID NO 36
<211> LENGTH: 29
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 36
catccagcag ggctcttctg agtcgtctc                                           29

<210> SEQ ID NO 37
<211> LENGTH: 30
<212> TYPE: DNA
<213> ORGANISM: Artificial
<220> FEATURE:
<223> OTHER INFORMATION: Oligonucletide designed to act as primer for
```

```
                    amplifying mutant TLR4 cDNA.

<400> SEQUENCE: 37
cctgctggat ggtagatcat ggaatccaga                                              30

<210> SEQ ID NO 38
<211> LENGTH: 30
<212> TYPE: DNA
<213> ORGANISM: Artificial
<220> FEATURE:
<223> OTHER INFORMATION: Oligonucletide designed to act as primer for
      amplifying mutant TLR4 cDNA.

<400> SEQUENCE: 38
tctggattcc atgatctacc atccagcagg                                              30
```

SCREENING METHOD FOR A SUBSTANCE THAT BINDS TO AN INTRACELLULAR REGION OF TLR4

TECHNICAL FIELD

The present invention relates to a method of screening for a drug for the prophylaxis or treatment of cardiac disease, autoimmune disease, inflammatory disease, central nervous system disease, infectious disease, sepsis, severe sepsis or septic shock.

BACKGROUND ART

Patent reference 1 describes that (i) a compound represented by the formula:

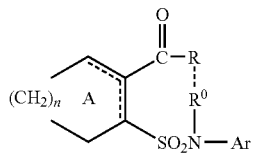

wherein R is an aliphatic hydrocarbon group optionally having substituent(s), an aromatic hydrocarbon group optionally having substituent(s), a heterocyclic group optionally having substituent(s), a group represented by the formula: —OR$^1$ (wherein R$^1$ is a hydrogen atom or an aliphatic hydrocarbon group optionally having substituent(s)), or a group represented by the formula:

wherein R$^{1b}$ is a hydrogen atom or an aliphatic hydrocarbon group optionally having substituent(s), and R$^{1c}$ is the same as or different from R$^{1b}$ and is a hydrogen atom or an aliphatic hydrocarbon group optionally having substituent(s), R$^0$ is a hydrogen atom or an aliphatic hydrocarbon group, or R$^1$ and R$^0$ form a bond with each other, ring A is a cycloalkene substituted by 1 to 4 substituents selected from (1) an aliphatic hydrocarbon group optionally having substituent(s), (2) an aromatic hydrocarbon group optionally having substituent(s), (3) a group represented by the formula: —OR$^{11}$ (wherein R$^{11}$ is a hydrogen atom or an aliphatic hydrocarbon group optionally having substituent(s)) and (4) a halogen atom, Ar is an aromatic hydrocarbon group optionally having substituent(s), a group represented by the formula:

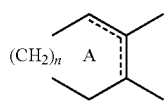

is a group represented by the formula:

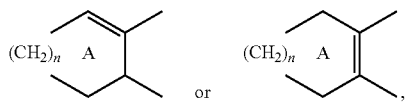

and n is an integer of 1 to 4, and (ii) a compound represented by the formula:

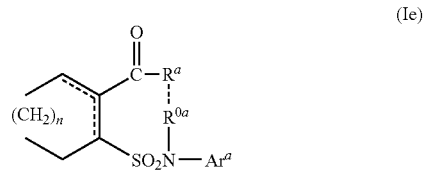

(Ie)

wherein R$^a$ is an aliphatic hydrocarbon group optionally having substituent(s), an aromatic hydrocarbon group optionally having substituent(s), a heterocyclic group optionally having substituent(s), a group represented by the formula: —OR$^{1a}$ (wherein R$^{1a}$ is a hydrogen atom or an aliphatic hydrocarbon group optionally having substituent(s)) or a group represented by the formula:

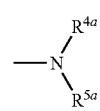

wherein R$^{4a}$ and R$^{5a}$ are the same or different and each is a hydrogen atom or an aliphatic hydrocarbon group optionally having substituent(s), R$^{0a}$ is a hydrogen atom or an aliphatic hydrocarbon group, or R$^a$ and R$^{0a}$ form a bond with each other, Ar$^a$ is an aromatic hydrocarbon group optionally having substituent (s), a group represented by the formula:

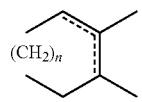

is a group represented by the formula:

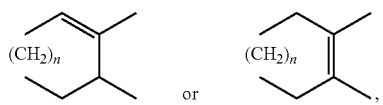

and n is an integer of 1 to 4, a salt thereof and a prodrug thereof; and patent reference 2 describes that a compound represented by the formula:

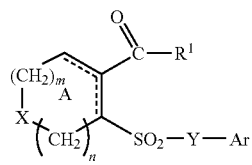

wherein $R^1$ is an aliphatic hydrocarbon group optionally having substituent(s), an aromatic hydrocarbon group optionally having substituent(s), a heterocyclic group optionally having substituent(s), a group represented by the formula: —$OR^{1a}$ (wherein $R^{1a}$ is a hydrogen atom or an aliphatic hydrocarbon group optionally having substituent(s)) or a group represented by the formula:

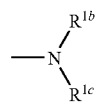

wherein $R^{1b}$ and $R^{1c}$ are the same or different and each is a hydrogen atom or an aliphatic hydrocarbon group optionally having substituent(s),
X is a methylene group, NH, a sulfur atom or an oxygen atom, Y is a methylene group optionally having substituent(s) or NH optionally having substituent(s),
ring A is a 5- to 8-membered ring optionally having 1 to 4 substituents selected from the group consisting of (1) an aliphatic hydrocarbon group optionally having substituent(s), (2) an aromatic hydrocarbon group optionally having substituent(s), (3) a group represented by the formula: —$OR^2$ (wherein $R^2$ is a hydrogen atom or an aliphatic hydrocarbon group optionally having substituent(s)) and (4) a halogen atom, Ar is an aromatic hydrocarbon group optionally having substituent(s),
a group represented by the formula:

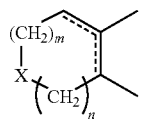

is a group represented by the formula:

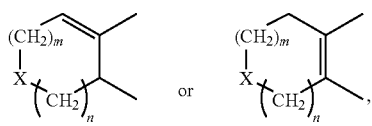

m is an integer of 0 to 2,
n is an integer of 1 to 3, and
the total of m and n is not more than 4;
provided that when X is a methylene group, Y is a methylene group optionally having substituent(s), a salt thereof and a prodrug thereof have a nitric oxide (NO) production-inhibitory effect and an inhibitory effect on the production of inflammatory cytokines, such as TNF-α, IL-1, IL-6 and the like, and are useful as agents for the prophylaxis or treatment of diseases including cardiac diseases, autoimmune diseases, inflammatory diseases, central nervous system diseases, infectious diseases, sepsis, septic shock and the like.

Patent reference 3 describes that the above-mentioned compounds are useful as TLR signal inhibitors or agents for the prophylaxis or treatment of severe sepsis.
patent reference 1: WO99/46242
patent reference 2: WO01/10826
patent reference 3: WO03/84527

DISCLOSURE OF THE INVENTION

Problems to be Solved by the Invention

The present invention aims to provide a method useful for screening for a drug for the prophylaxis or treatment of cardiac disease, autoimmune disease, inflammatory disease, central nervous system disease, infectious disease, sepsis, severe sepsis or septic shock. Furthermore, the present invention aims to provide a kit useful for screening for a drug for the prophylaxis or treatment of the above-mentioned diseases.

Means of Solving the Problems

The present inventors have conducted intensive studies in an attempt to solve the aforementioned problems and found that a cycloalkene compound having a TLR4 signal transduction-inhibitory action and useful as a therapeutic drug for sepsis and the like unexpectedly binds to an intracellular region of TLR4. The present inventors have further studied based on this finding and completed the present invention.
Accordingly, the present invention relates to
[1] a method of screening for a drug for the prophylaxis or treatment of at least one disease selected from the group consisting of cardiac disease, autoimmune disease, inflammatory disease, central nervous system disease, infectious disease, sepsis, severe sepsis and septic shock, which comprises selecting a substance that binds to an intracellular region of TLR4, and inhibits signal transduction from said molecule,
[2] the method of the above-mentioned [1], wherein the binding site consists of one or more cysteine residues in a region shown by amino acid Nos. 652-839 of the amino acid sequence shown by SEQ ID NO: 2,
[3] the method of the above-mentioned [2], wherein the binding site consists of cysteine residue(s) at the 706th and/or the 747th of the amino acid sequence shown by SEQ ID NO: 2,
[4] the method of the above-mentioned [1], comprising the following steps (1) to (4):
(1) preparing a cell that expresses TLR4 or an intracellular region thereof and contains a gene under regulation of a promoter containing an NF-κB or IRF3 binding sequence (sample 1), and a cell that expresses a protein wherein one or more cysteine residues or amino acids adjacent thereto in an intracellular region of TLR4 have been mutated to other amino acids or an intracellular region of said protein and contains a gene under regulation of a promoter containing an NF-κB or IRF3 binding sequence (sample 2),
(2) culturing sample 1 and sample 2 each in the presence of a test compound,
(3) measuring the expression of the gene in sample 1 and sample 2 after culture,
(4) selecting, when the level of gene expression in sample 1 decreases by not less than about 20% than that in sample 2, the test compound as a substance that binds to said molecule in the intracellular region of TLR4 to inhibit signal transduction from the molecule,

[5] the method of the above-mentioned [4], wherein the cysteine residue is cysteine residue(s) at the 706th and/or the 747th of the amino acid sequence shown by SEQ ID NO: 2,

[6] the method of the above-mentioned [4], wherein the gene is a reporter gene,

[7] a screening kit for selecting a substance that binds to an intracellular region of TLR4 and inhibits signal transduction from said molecule, comprising the following constitutions (1)-(2):

(1) a cell that expresses TLR4 or an intracellular region thereof and contains a gene under regulation of a promoter containing an NF-κB or IRF3 binding sequence, (2) a cell that expresses a protein wherein one or more cysteine residues or amino acids adjacent thereto in an intracellular region of TLR4 have been mutated to other amino acids or an intracellular region thereof and contains a gene under regulation of a promoter containing NF-κB or IRF3 binding sequence, and

[8] the screening kit of the above-mentioned [7], wherein the substance is a drug for the prophylaxis or treatment of at least one disease selected from the group consisting of cardiac disease, autoimmune disease, inflammatory disease, central nervous system disease, infectious disease, sepsis, severe sepsis and septic shock.

Effect of the Invention

The screening method of the present invention affords an effect that a substance having an activity of preventing or treating cardiac disease, autoimmune disease, inflammatory disease, central nervous system disease, infectious disease, sepsis, severe sepsis or septic shock can be efficiently selected by evaluating the binding of a test compound with an intracellular region of TLR4, as well as inhibition of signal transduction from said receptor as a result of the binding.

BRIEF DESCRIPTION OF THE DRAWINGS

FIG. 3 shows the expression levels of luciferase gene under the control of NF-.kappa.B, which are obtained by culturing the cells that express wild-type TLR4 and various mutant TLR4s, in the presence or absence of compound A (FIG. 3A), compound B (FIG. 3B), compound C (FIG. 3C) and compound D (FIG. 3D) after LPS stimulation. WT: wild-type TLR4; 1CA: TLR4.sup.C666A; 2CA: TLR.sup.C706A; 3CA: TLR4.sup.C747A; 4CA: TLR.sup.C831A; PH: TLR.sup.P714H; 1KR: TLR.sup.K653R; 2KR: TLR.sup.K666R; 3KR: TLR.sup.K694R; 4KR: TLR.sup.K729R; 5KR: TLR.sup.K732R; 6KR: TLR.sup.K773R; 7KR: TLR.sup.K77R; 8KR: TLR.sup.K813R; 9KR: TLR.sup.K819R; EV: vector alone.

Figure 1:
FIG. 1 shows CBB stained image (A) and autoradiograph (B) of gel electrophoresis of reaction products of $^3$H-labeled compound A with fusion proteins of GST and TIRAP, GST and TIR domain of TLR2 and GST and TIR domain of TLR4. Lane 1: GST; Lane 2: GST-TIRAP fusion protein; Lane 3: GST-TLR2 intracellular TIR domain fusion protein; Lane 4: GST-TLR4 intracellular TIR domain fusion protein

The screening method of the present invention comprises selecting a substance that binds to an intracellular region of TLR4, and inhibits signal transduction by TLR4.

TLR4 is single-spanning transmembrane receptor, and has an extracellular region, a transmembrane region and an intracellular region from the N-terminal side. The "intracellular region of TLR4" means, in the case of human TLR4 shown by SEQ ID NO: 2, for example, a region consisting of an amino acid sequence of amino acid Nos. 652-839.

The "inhibition of signal transduction by TLR4" may be inhibition of any process of signal transduction from TLR4, as long as it does not result in the induction of NF-κB dependent inflammatory cytokine or induction of expression of IRF3 dependent interferon and interferon-derived gene.

The substance that inhibits signal transduction by TLR4, which is selected by the screening method of the present invention, may be bound with any part of an intracellular region of TLR4, and may be bound with one part or plural parts of the intracellular region. Preferably, the signal inhibitory substance binds to one or more cysteine residues in an intracellular region of TLR4 (e.g., in the case of human TLR4 shown by SEQ ID NO: 2, cysteine residues at the 664th, the 706th, the 747th and the 831st of the amino acid sequence), more preferably, one or more cysteine residues in Toll-IL-1 receptor (TIR) domain (e.g., in the case of human TLR4, a region shown by 674th-839th amino acids of the amino acid sequence shown by SEQ ID NO: 2) that activates signal pathway in the cytoplasm, more preferably, the cysteine residue(s) at the 706th and/or the 747th amino acid(s) of the sequence shown by SEQ ID NO: 2.

The screening method of the present invention comprising selecting a substance that inhibits signal transduction by TLR4 by binding to an intracellular region of this molecule characteristically uses a polypeptide containing whole or partial intracellular region of TLR4.

The above-mentioned polypeptide to be used for the screening method of the present invention may be any as long as it contains at least a binding site targeted by the objective signal transduction inhibitory substance, and the binding site can be freely set within the intracellular region of TLR4. Preferred is the above-mentioned cysteine residue. More preferably, therefore, the polypeptide to be used for the screening method of the present invention is a polypeptide containing a partial amino acid sequence of the amino acid sequence shown by SEQ ID NO: 2, which partial sequence comprises at least a cysteine residue(s) at the 706th and/or the 747th of the amino acid sequence. The length of the polypeptide is not particularly limited as long as it contains an adjacent amino acid sequence sufficient for the objective signal transduction inhibitory substance to bind to the target binding site. For example, the length is 10 or more amino acids, preferably 50 or more amino acids, more preferably 100 or more amino acids, more preferably 200 or more amino acids. While the upper limit of the polypeptide length is not particularly limited, it is, for example, full-length of TLR4 (in the case of human TLR4, 839 amino acids (containing signal peptide)) and the like.

For example, when the length of the polypeptide is shortened, the binding site of the signal transduction inhibitory substance is easily specified. However, the polypeptide often lacks signal transduction ability. Accordingly, the test compound bound with the polypeptide needs to be separately tested for the presence or absence of signal transduction inhibitory action. For simultaneous detection of the binding of the test compound with the target site, and the signal transduction inhibitory action, the polypeptide to be used in the present invention needs to contain at least a region necessary for signal transduction by TLR4. For example, a polypeptide containing the above-mentioned TIR domain, a polypeptide containing the whole intracellular region, a polypeptide containing a transmembrane region, full-length TLR4 and the like are desirable. In this case, whether or not the test compound binds to the desired target site can be determined by, as mentioned below, deleting the amino acid at the target site, or producing a polypeptide substituted by other amino acid and examining the presence or absence of the binding ability of the test compound to the polypeptide.

To facilitate detection of the binding of polypeptide and the test compound, the polypeptide may be provided as a fusion polypeptide having a tag on the N terminal or C terminal. Examples of such tag include GST tag, His tag, MBP tag, Flag tag and the like. A polypeptide having such tag sequence can be pulled down using glutathione, metal chelate, maltose or anti-Flag antibody carrier. By labeling the test compound with RI (e.g., $^{3}H$, $^{35}S$, $^{32}P$ etc.) and the like, the binding of the test compound to polypeptide can be detected more easily based on the measurement of the label on such carrier.

The TLR4 protein in the present invention is a protein comprising the same or substantially the same amino acid sequence as an amino acid sequence shown by SEQ ID NO: 2.

The TLR4 protein may be a protein derived from a cell (e.g., splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immune cell (e.g., macrophage, T cell, B cell, natural killer cell, mast cell, neutrophil, basophil, eosinophil, monocyte, dendritic cell), megakaryocyte, synovial cell, chondrocyte, bone cell, osteoblast, osteoclast, mammary gland cell, hepatocyte, interstitial cell, or a corresponding precursor cell, stem cell or cancer cell thereof, and the like) of warm-blooded animals (e.g., human, mouse, rat, guinea pig, hamster, rabbit, sheep, goat, swine, bovine, horse, bird, cat, dog, monkey, chimpanzee and the like) or any tissue in which these cells are present [e.g., brain or any portion of brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine and small intestine), blood vessel, heart, thymus, spleen, submandibular gland, peripheral blood, prostate, testicle, ovary, placenta, uterus, bone, joint, adipose tissue, skeletal muscle, peritoneum and the like]. The TLR4 protein may also be a chemically synthesized protein or a protein synthesized using a cell-free translation system. Alternatively, the TLR4 protein may be a recombinant protein produced by a transformant introduced with a nucleic acid having the base sequence that encodes the above-described amino acid sequence.

As "substantially the same amino acid sequence" as an amino acid sequence shown by SEQ ID NO: 2, an amino acid sequence having a homology of about 70% or more, preferably about 80% or more, more preferably about 90% or more, particularly preferably about 95% or more, and most preferably about 98% or more, with an amino acid sequence shown by SEQ ID NO: 2 can be mentioned. Here, the "homology" means a ratio (%) of identical amino acid residues and similar amino acid residues to all overlapping amino acid residues in the best alignment where two amino acid sequences are aligned using a mathematical algorithm known in the technical field (preferably, the algorithm considers introduction of gaps on one or both sides of the sequence for the best alignment). "A similar amino acid" means an amino acid having similar physiochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Substitution by such similar amino acids is expected to give no change in the phenotype of protein (i.e., constitutive amino acid substitution). Specific examples of constitutive amino acid substitution are obvious in the relevant technical field, and are described in various documents (see, for example, Bowie et al., Science, 247:1306-1310 (1990)).

Homology of the amino acid sequences in the present specification can be calculated under the following conditions (an expectation value=10; gaps are allowed; matrix=BLOSUM62; filtering=OFF) using a homology scoring algorithm NCBI BLAST (National Center for Biotechnology Information Basic Local Alignment Search Tool). As other algorithm for determining the homology of amino acid sequence, for example, the algorithm described in Karlin et al., *Proc. Natl. Acad. Sci. USA*, 90: 5873-5877 (1993) [the algorithm is incorporated in NBLAST and XBLAST program (version 2.0) (Altschul et al., *Nucleic Acids Res.*, 25: 3389-3402 (1997))], the algorithm described in Needleman et al., *J. Mol. Biol.*, 48: 444-453 (1970) [the algorithm is incorporated in the GAP program in GCG software package], the algorithm described in Myers and Miller, *CABIOS*, 4: 11-17 (1988) [the algorithm is incorporated in ALIGN program (version 2.0) which is a part of the CGC sequence alignment software package], the algorithm described in Pearson et al., *Proc. Natl. Acad. Sci. USA*, 85: 2444-2448 (1988) [the algorithm is incorporated in the FASTA program in GCG software package] and the like can be mentioned, and they can be preferably used in a similar way.

More preferably, the "substantially the same amino acid sequence" is an amino acid sequence having an identity of about 70% or more, preferably about 80% or more, more preferably about 90% or more, particularly preferably about 95%, most preferably about 98% or more, with an amino acid sequence shown by SEQ ID NO: 2.

"The protein having substantially the same amino acid sequence" as an amino acid sequence shown by SEQ ID NO: 2 refers a protein that comprises substantially the same amino acid sequence as the aforementioned amino acid sequence shown by SEQ ID NO: 2, and that has substantially the same quality of activity as a protein that comprises an amino acid sequence shown by SEQ ID NO: 2.

The "substantially the same quality of activity" refers to (1) signal transduction activity (that is, activity to activate NF-κB and/or IRF3 by LPS stimulation, and induce expression of inflammatory cytokine and/or interferon and interferon induced gene), and (2) binding activity to a compound that binds to an intracellular region of TLR4 to inhibit the above-mentioned signal transduction. Substantially the same quality means that the activities thereof are qualitatively equivalent to each other. Accordingly, signal transduction activity and binding activity to a signal transduction inhibitory substance are preferably equivalent. However, quantitative factors such as the extent of these activities and the molecular weights of the proteins may be different (e.g., differences within the range of about 0.01 to 100 times, preferably about 0.1 to 10 times, more preferably 0.5 to 2 times, with respect to activity).

The signal transduction activity of TLR4 can be measured by, but not limited to, a known method, for example, measurement of variation of expression of inflammatory cytokines (e.g., TNFα, IL-1, IL-6, IFN-γ etc.), interferons (IFN-β, IFN-α) or interferon induced genes (e.g., IP-10, GARG16, IRG-1 etc.) in TLR4 expression cells, and measurement of activation of transcription factors (e.g., NF-κB, IRF3, AP-1, C/EBP) using, as an index, expression of a reporter gene under control of a promoter containing a cis-element specific to such transcription factor. On the other hand, the binding activity to a signal transduction inhibitory substance can be measured, for example, using the aforementioned pull down assay, surface plasmon resonance (SPR), fluorescence energy transfer and the like. Alternatively, the binding activity of the test compound and signal transduction inhibition can also be evaluated altogether by, as mentioned below, deleting the amino acid of a desired target site or separately preparing mutant polypeptide substituted by other amino acid, and measuring the signal transduction activity in the presence of a test compound for each of the wild-type polypeptide and mutant polypeptide, as mentioned above.

The TLR4 to be used in the present invention includes, for example, a protein having (1) an amino acid sequence shown by SEQ ID NO: 2, wherein one or more (e.g., about 1-50, preferably about 1-30, more preferably about 1-10, more preferably about 1-5) amino acids have been deleted, (2) an amino acid sequence shown by SEQ ID NO: 2, wherein one or more (e.g., about 1-50, preferably about 1-30, more preferably about 1-10, more preferably about 1-5) amino acids have been added, (3) an amino acid sequence shown by SEQ ID NO: 2, wherein one or more (e.g., about 1-50, preferably about 1-30, more preferably about 1-10, more preferably about 1-5) amino acids have been inserted, (4) an amino acid sequence shown by SEQ ID NO: 2, wherein one or more (e.g., about 1-50, preferably about 1-30, more preferably about 1-10, more preferably about 1-5) amino acids have been substituted by other amino acid(s), or (5) an amino acid sequence which is a combination thereof.

When one or more amino acids are to be deleted, the deletion site is a site other than the binding site of a desired signal transduction inhibitory substance, preferably a site other than the cysteine residue and adjacent site thereof in an intracellular region. When one or more amino acids are to be inserted or substituted by other amino acid(s), it is a site other than the binding site of a desired signal transduction inhibitory substance (preferably a site other than the cysteine residue and adjacent site thereof in an intracellular region), and when it is said site, the site should not affect the quality of the activity of the site (that is, binding activity to a TLR4 signal transduction inhibitory substance that binds to the site), as a result of the insertion or substitution.

For the proteins and peptides described in the present specification, the left end indicates the N-terminus (amino terminus) and the right end indicates the C-terminus (carboxyl terminus), according to the common practice of peptide designation. For TLR4 used for the screening method of the present invention, the C-terminus may be any of a carboxyl group (—COOH), a carboxylate (—COO$^-$), an amide (—CONH$_2$) or an ester (—COOR).

Here, as R in the ester, a $C_{1-6}$ alkyl group such as methyl, ethyl, n-propyl, isopropyl and n-butyl, a $C_{3-8}$ cycloalkyl group such as cyclopentyl and cyclohexyl, a $C_{6-12}$ aryl group such as phenyl and α-naphthyl, a phenyl-$C_{1-2}$ alkyl group such as benzyl and phenethyl, a $C_{7-14}$ aralkyl group such as an α-naphthyl-$C_{1-2}$ alkyl group such as α-naphthylmethyl, a pivaloyloxymethyl group; and the like can be used.

When the TLR4 has a carboxyl group (or a carboxylate) in addition to that on the C-terminal, one in which the carboxyl group is amidated or esterified is also included in the TLR4 in the present invention. In this case, as the ester, the above-described C-terminal ester and the like, for example, can be used.

Furthermore, the TLR4 also includes a protein wherein the amino group of the N-terminal amino acid residue thereof (e.g., methionine residue) is protected by a protecting group (e.g., a $C_{1-6}$ acyl group such as $C_{1-6}$ alkanoyl such as a formyl group or an acetyl group, and the like), a protein wherein the N-terminal glutamine residue, which is produced by cleavage in vivo, has been converted to pyroglutamic acid, a protein wherein a substituent (e.g., —OH, —SH, an amino group, an imidazole group, an indole group, a guanidino group and the like) on an amino acid side chain in the molecule is protected by an appropriate protecting group (e.g., a $C_{1-6}$ acyl group such as a $C_{1-6}$ alkanoyl group such as a formyl group or an acetyl group, and the like), a conjugated protein such as what is called a glycoprotein, which has a sugar chain bound thereto, and the like.

The partial peptide of TLR4 to be used in the present invention has the above-mentioned partial amino acid sequence of TLR4 (that is, partial or whole sequence of intracellular region), and has substantially the same activity with TLR4. Here, the "substantially the same quality of activity" means a binding activity to a compound that binds to an intracellular region of TLR4 to inhibit the above-mentioned signal transduction. Preferably, the partial peptide further retains a signal transduction activity (that is, activity to activate NF-κB and/or IRF3 by LPS stimulation, and induce expression of inflammatory cytokine and/or interferon and interferon induced gene). The "substantially the same quality of activity" can be measured by a method similar to the method mentioned above for TLR4.

In the present specification, the TLR4 protein and the partial peptide are hereinafter sometimes to be referred to as "inhibitory substance binding type polypeptide".

For the partial peptide of the TLR4, the C-terminus may be any of a carboxyl group (—COOH), a carboxylate (—COO$^-$), an amide (—CONH$_2$) or an ester (—COOR). Here, as R in the ester, the same as those mentioned for the TLR4 can be mentioned. When these peptides have a carboxyl group (or a carboxylate) in addition to that on the C-terminal, one in which the carboxyl group is amidated or esterified is also included in the partial peptide of the present invention. In this case, as the ester, the above-described C-terminal ester and the like, for example, can be used.

Furthermore, the partial peptide of the TLR4, like the foregoing TLR4, also includes a partial peptide wherein the N-terminal methionine residue is protected by a protecting group, a partial peptide wherein Gln, which is produced upon cleavage at the N-terminal in vivo, has been converted to pyroglutamic acid, a partial peptide wherein a substituent on a side chain of an amino acid in the molecule is protected by an appropriate protecting group, a conjugated peptide such as what is called a glycopeptide having a sugar chain bound thereto, and the like.

TLR4 and a partial peptide thereof may be in a free form or a salt. Examples of the salts of TLR4 or a partial peptide thereof include physiologically acceptable salts with acids or bases, and physiologically acceptable acid addition salts are particularly preferable. Such salts include, for example, salts with inorganic acids (e.g., hydrochloric acid, phosphoric acid, hydrobromic acid, sulfuric acid), or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

In TLR4 or a partial peptide thereof, a polypeptide wherein the binding site of a desired signal transduction inhibitory substance (preferably a cysteine residue in an intracellular region, for example, in human TLR4 shown by SEQ ID NO: 2, one or more cysteine residues at the 664th, the 706th, the 747th and the 831st of the amino acid sequence, more preferably cysteine residue(s) at the 706th and/or the 747th) is deleted or substituted by other amino acids (e.g., alanine, glycine, valine, leucine, isoleucine and the like, but not limited to these, preferably alanine) does not have a binding activity to the objective signal transduction inhibitory substance. Hence, even when the polypeptide is contacted with a compound that specifically binds to the target binding site to inhibit signal transduction, it does not bind to the compound. In addition, when the mutant partial peptide further retains a signal transduction activity, signal transduction is not inhibited even when the target binding site is contacted with a compound that specifically binds to the target binding site to inhibit signal transduction.

In the present specification, the mutant TLR and mutant partial peptide are sometimes referred to as hereinafter "inhibitory substance non-binding type polypeptide".

TLR4 or a salt thereof can also be produced from the cells or tissues of the above-described warm-blooded animals by a method of protein purification known per se. Specifically, TLR4 or a salt thereof can be produced by homogenizing a tissue or cells of a warm-blooded animal, and separating and purifying a soluble fraction by chromatographies such as reversed-phase chromatography, ion exchange chromatography, affinity chromatography and the like.

TLR4 and a partial peptide thereof can also be produced according to known peptide synthesis method.

The method of peptide synthesis may be any of, for example, a solid phase synthesis process and a liquid phase synthesis process. That is, a desired protein can be produced by condensing a partial peptide or amino acids capable of constituting the TLR4 and the remaining portion, and eliminating any protecting group the resultant product may have.

As examples of the commonly known methods of condensation and elimination of the protecting group, the methods described in (1) to (5) below can be mentioned.
(i) M. Bodanszky and M. A. Ondetti, Peptide Synthesis, Interscience Publishers, New York (1966)
(ii) Schroeder and Luebke, The Peptide, Academic Press, New York (1965)
(iii) Nobuo Izumiya, et al.: Peptide Gosei-no-Kiso to Jikken, published by Maruzen Co. (1975);
(iv) Haruaki Yajima and Shunpei Sakakibara: Seikagaku Jikken Koza 1, Tanpakushitsu no Kagaku IV, 205 (1977)
(v) Haruaki Yajima, ed.: Zoku Iyakuhin no Kaihatsu, Vol. 14, Peptide Synthesis, published by Hirokawa Shoten.

TLR4 or a partial peptide thus obtained can be isolated and purified by a known purification method. Examples of the purification method include solvent extraction, distillation, column chromatography, liquid chromatography, recrystallization and a combination of these.

When the TLR4 or a partial peptide thereof obtained by the above-described method is a free form, the free form can be converted to an appropriate salt by a publicly known method or a method based thereon; conversely, when the TLR4 or a partial peptide thereof is obtained in the form of a salt, the salt can be converted to a free form or another salt by a publicly known method or a method based thereon.

For the synthesis of the TLR4 or a partial peptide thereof, an ordinary commercially available resin for protein synthesis can be used. As examples of such resins, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2', 4,-dimethoxyphenyl-hydroxymethyl)phenoxy resin, 4-(2',4'-dimethoxyphenyl-Fmoc-aminoethyl)phenoxy resin and the like can be mentioned. Using such a resin, an amino acid having an appropriately protected α-amino group and side chain functional group is condensed on the resin in accordance with the sequence of the desired protein or peptide according to various methods of condensation known per se. At the end of the reaction, the protein (peptide) is cleaved from the resin, various protecting groups are removed simultaneously, and a reaction to form an intramolecular disulfide bond is carried out in a highly diluted solution to obtain the desired protein (peptide) or an amide thereof.

For the above-described condensation of protected amino acids, various activation reagents useful for protein synthesis can be used, with preference given to a carbodiimide. As the carbodiimide, DCC, N,N'-diisopropylcarbodiimide, N-ethyl-N'-(3-dimethylaminoprolyl)carbodiimide and the like can be used. For the activation using these carbodiimides, the protected amino acid, along with a racemation-suppressing additive (e.g., HOBt, HOOBt), may be added directly to the resin, or the protected amino acid may be activated in advance as a symmetric acid anhydride, or HOBt ester or HOOBt ester and then added to the resin.

A solvent used for activation of protected amino acids and condensation of protected amino acids with a resin can be appropriately selected from among solvents that are known to be usable for protein condensation reactions. Examples of such useful solvents include acid amides such as N,N-dimethylformamide, N,N-dimethylacetamide, and N-methylpyrrolidone; halogenated hydrocarbons such as methylene chloride and chloroform; alcohols such as trifluoroethanol; sulfoxides such as dimethyl sulfoxide; amines such as pyridine; ethers such as dioxane and tetrahydrofuran; nitrites such as acetonitrile and propionitrile; esters such as methyl acetate and ethyl acetate; suitable mixtures thereof; and the like. Reaction temperature is appropriately selected from the range that is known to be usable in peptide binding reactions, and is normally from the range of about −20° C. to about 50° C. An activated amino acid derivative is normally used from 1.5 to 4 times in excess. When the condensation is insufficient as the result of the test using a ninhydrin reaction, sufficient condensation can be carried out by repeating the condensation reaction without elimination of the protecting group. If the condensation is insufficient even though the condensation reaction is repeated, unreacted amino acids can be acetylated by using acetic anhydride or acetylimidazole.

A protecting method and a protecting group of a functional group that should not been involved in the reaction of starting materials, a method of removing the protecting group, a method of activating a functional group involved in the reaction, and the like can be appropriately selected from among publicly known groups or publicly known means.

As the protecting group for the amino group of the starting material, for example, Z, Boc, tertiary pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulfenyl, diphenylphosphinothioyl, Fmoc and the like can be used.

The carboxyl group can be protected by, for example, alkyl esterification (e.g., linear, branched or cyclic alkyl esterification with methyl, ethyl, propyl, butyl, tertiary butyl, cyclopentyl, cyclohexyl, cycloheptyl, cyclooctyl, 2-adamantyl, and the like), aralkyl esterification (e.g., benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, tertiary butoxycarbonyl hydrazidation, trityl hydrazidation, and the like.

The hydroxyl group of serine can be protected by, for example, esterification or etherification. As the group suitable for this esterification, for example, lower alkanoyl groups such as an acetyl group, aroyl groups such as a benzoyl group, and groups derived from carbonic acid such as benzyloxycarbonyl group, ethoxycarbonyl group and the like can be used. In addition, as examples of the group suitable for etherification, for example, a benzyl group, a tetrahydropyranyl group, a t-butyl group and the like can be mentioned.

As the protecting group for the phenolic hydroxyl group of tyrosine, for example, Bzl, Cl$_2$-Bzl, 2-nitrobenzyl, Br—Z, tertiary butyl and the like can be used.

As the protecting group for the imidazole of histidine, for example, Tos, 4-methoxy-2,3,6-trimethylbenzenesulfonyl, DNP, benzyloxymethyl, Bum, Boc, Trt, Fmoc and the like can be used.

As the method of removing (eliminating) a protecting group, catalytic reduction in a hydrogen stream in the presence of a catalyst such as Pd-black or Pd-carbon; acid treatment by means of anhydrous hydrogen fluoride, methanesulfonic acid, trifluoromethane-sulfonic acid, trifluoroacetic acid, or a mixture solution thereof; base treatment by means of diisopropylethylamine, triethylamine, piperidine, piperazine or the like; and reduction with sodium in liquid ammonia, and the like, for example, can be used. The elimination reaction by the above-described acid treatment is generally carried out at a temperature of about −20° C. to about 40° C.; the acid treatment is efficiently conducted by adding a cation scavenger such as, for example, anisole, phenol, thioanisole, m-cresol, p-cresol, dimethyl sulfide, 1,4-butanedithiol or 1,2-ethanedithiol. Also, a 2,4-dinitrophenyl group used as a protecting group for the imidazole of histidine is removed by thiophenol treatment; a formyl group used as a protecting group for the indole of tryptophan is removed by acid treatment in the presence of 1,2-ethanedithiol, 1,4-butanedithiol, or the like, as well as by alkali treatment with a dilute sodium hydroxide solution, dilute ammonia, or the like.

As the starting material having an activated carboxyl group, for example, a corresponding acid anhydride, an azide, an activated ester [an ester with an alcohol (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, or HOBt)] and the like can be used. As the starting material having an activated amino group, for example, a corresponding phosphoric amide can be used.

As another method for obtaining an amide of a protein (peptide), for example, a method comprising protecting the α-carboxyl group of each C-terminal amino acid of partial peptide constituting a protein (peptide) by amidation, extending peptide chain to the amino group side in a desired chain length (amino acid to be joined with C-terminal amino acid of adjacent partial peptide). Producing a peptide only without α-amino-protecting group of N-terminal amino acid of C-terminal side peptide chain, and a peptide only without carboxyl group-protecting group of C-terminal amino acid of N-terminal side peptide chain, and condensing these peptides in the above-mentioned mixed solvent can be mentioned. The details of the condensation reaction are as mentioned above. After purification of the protected protein (protected peptide) obtained by condensation, the protecting group is eliminated by the above-mentioned method to give a desired crude protein (crude peptide). The crude protein (crude peptide) is purified by various known purification means, and the main fraction is lyophilized to give an amide of the desired protein (peptide).

An ester of the protein (peptide) can be obtained, for example, by condensing the α-carboxyl group of C-terminal amino acid with a desired alcohol to give an amino acid ester, and treating the ester in the same manner as in the above-mentioned amide.

The partial peptide of the TLR4 or a salt thereof can also be produced by cleaving the TLR4 or a salt thereof with an appropriate peptidase.

Moreover, a TLR4 or a partial peptide thereof can also be produced by culturing a transformant having the nucleic acid encoding same, and separating and purifying a TLR4 or a partial peptide thereof from the obtained culture.

The nucleic acid that encodes TLR4 or a partial peptide thereof may be DNA or RNA, or a DNA/RNA chimera, and is preferably DNA. In addition, the nucleic acid may be a double-strand, or single-strand. The double-strand may be a double-stranded DNA, a double-stranded RNA, or a DNA: RNA hybrid. In the case of a single strand, it may be a sense strand (i.e., coding strand) or an antisense strand (i.e., non-coding strand).

As the DNA encoding a TLR4 or a partial peptide thereof, genomic DNA, cDNA derived from any cell [for example, splenocyte, nerve cell, glial cell, pancreatic β cells, myeloid cell, mesangial cell, Langerhans' cell, epidermal cell, epithelial cell, endothelial cell, fibroblast, fibrocyte, myocytes, adipocyte, immune cell (e.g., macrophage, T cell, B cell, natural killer cell, mast cell, neutrophil, basophil, eosinophils, monocyte, dendritic cell), megakaryocyte, synovial cell, chondrocytes, bone cell, osteoblast, osteoclast, mammary cell, hepatocyte or interstitial cell, or a corresponding precursor cell, stem cell, cancer cell and the like, blood cells] of warm-blooded animal (e.g., human, mouse, rat, guinea pig, hamster, rabbit, sheep, goat, swine, bovine, horse, bird, cat, dog, monkey, chimpanzee and the like), or any tissue where such cells are present [e.g., brain or any portion of brain (e.g., olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, lateral lobe, putamen, caudate nucleus, callosum, substantia nigra), spinal cord, hypophysis, stomach, pancreas, kidney, liver, gonad, thyroid, gallbladder, bone marrow, adrenal gland, skin, muscle, lung, gastrointestinal tract (e.g., large intestine, small intestine), blood vessel, heart, thymus, spleen, submandibular gland, peripheral blood, peripheral blood cell, prostate, testicle, ovary, placenta, uterus, bone, joint, adipose tissue, peritoneum and the like], synthetic DNA and the like can be mentioned. A genomic DNA and cDNA encoding TLR4 or a partial peptide thereof can also be directly amplified by Polymerase Chain Reaction (hereinafter to be abbreviated as "PCR method") or Reverse Transcriptase-PCR (hereinafter to be abbreviated as "RT-PCR method"), using genomic DNA fraction or total RNA or mRNA fraction prepared from the above-mentioned cell/tissue as a template. Alternatively, genomic DNA or cDNA encoding TLR4 or a partial peptide thereof can also be cloned by colony or plaque hybridization method, PCR method and the like, from the genomic DNA library or cDNA library prepared by inserting, into a suitable vector, a fragment of genomic DNA and total RNA or mRNA prepared from the above-mentioned cell/tissue. The vector to be used for the library may be any of bacteriophage, plasmid, cosmid, phagemid and the like.

An example of the DNA that encodes the TLR4 includes, a DNA that has a base sequence shown by SEQ ID NO: 1, a DNA that has a base sequence hybridizing to a complementary strand sequence of a base sequence shown by SEQ ID NO: 1 under high stringent conditions and encodes a protein having substantially the same quality of activity as the aforementioned protein comprising an amino acid sequence shown by SEQ ID NO: 2 (that is, the signal transduction activity and the binding activity to a TLR4 signal transduction inhibitory substance at the target binding site etc.) or the like.

Useful DNA capable of hybridizing with the complementary strand sequence of the base sequence shown by SEQ ID NO:1 under high stringent conditions include, for example, a DNA comprising a base sequence having a homology of about 60% or more, preferably about 70% or more, more preferably about 80% or more, particularly preferably about 90% or more, to the base sequence shown by SEQ ID NO:1.

Homology of the base sequences in the present specification can be calculated under the following conditions (an expectation value=10; gaps are allowed; filtering=ON; match score=1; mismatch score=−3) using a homology scoring algorithm NCBI BLAST (National Center for Biotechnology Information Basic Local Alignment Search Tool). As other algorithm with which to determine the homology of the base sequence, the homology calculation algorithm of the above-mentioned amino acid sequence can be preferably used in the same manner.

The hybridization can be performed by a method known per se or a method analogous thereto, for example, a method described in Molecular Cloning, 2nd ed. (J. Sambrook et al., Cold Spring Harbor Lab. Press, 1989) and the like. A commercially available library can also be used according to the instructions of the attached manufacturer's protocol. Preferably, the hybridization can be carried out under high stringent conditions.

High-stringent conditions refer to, for example, conditions involving a sodium salt concentration of about 19 to about 40 mM, preferably about 19 to about 20 mM, and a temperature of about 50 to about 70° C., preferably about 60 to about 65° C. In particular, a case wherein the sodium concentration is about 19 mM and the temperature is about 65° C. is preferred. Those skilled in the art can easily regulate the conditions to obtain a desired stringency by appropriately changing the salt concentration of hybridization solution, hybridization reaction temperature, probe concentration, probe length, number of mismatches, hybridization reaction time, salt concentration of washing solution, washing temperature, and the like.

The DNA encoding TLR4 is preferably human TLR4DNA having the base sequence shown by SEQ ID NO: 1, or its allele variant, or ortholog of other warm-blooded animal (e.g., mouse, rat, guinea pig, hamster, rabbit, sheep, goat, swine, bovine, horse, bird, cat, dog, monkey, chimpanzee and the like).

The DNA encoding inhibitory substance binding type polypeptide (partial peptide) may be any as long as it contains a base sequence encoding all or a part of the intracellular region of TLR4 [containing at least a target binding site (preferably a cysteine residue in an intracellular region, for example, in human TLR4 shown by SEQ ID NO: 2, one or more cysteine residues at the 664th, the 706th, the 747th and the 831st of the amino acid sequence, more preferably cysteine residue(s) at the 706th and/or the 747th) of the objective TLR4 signal transduction inhibitory substance].

In addition, the DNA encoding an inhibitory substance non-binding type polypeptide may be any as long as it contains a base sequence encoding TLR4 or a partial peptide thereof wherein a codon encoding a target binding site (preferably a cysteine residue in an intracellular region, for example, in human TLR4 shown by SEQ ID NO: 2, one or more cysteine residues at the 664th, the 706th, the 747th and the 831st of the amino acid sequence, more preferably cysteine residue(s) at the 706th and/or the 747th) of the objective TLR4 signal transduction inhibitory substance is deleted, or a base sequence substituted by a codon encoding other amino acids (e.g., alanine, glycine, valine, leucine, isoleucine etc., preferably alanine, though not limited thereto).

The DNA that encodes the TLR4 or a partial peptide thereof can be cloned by amplifying it by the PCR method using a synthetic DNA primer having a portion of the base sequence that encodes the protein or peptide, or by hybridizing DNA incorporated in an appropriate expression vector to a labeled DNA fragment or synthetic DNA that encodes a portion or the entire region of the protein of the present invention. The hybridization can be performed by, for example, a method described in Molecular Cloning, 2nd ed. (ibid.) and the like. A commercially available library can also be used according to the instructions of the manufacturer's protocol attached thereto.

The base sequence of the DNA can be converted according to a method known per se, such as the ODA-LA PCR method, the Gapped duplex method, or the Kunkel method, or a method based thereon, using a commonly known kit, for example, Mutan™-super Express Km (TAKARA SHUZO CO. LTD.), Mutan™-K (TAKARA SHUZO CO. LTD.) and the like. Accordingly, the DNA encoding an inhibitory substance non-binding type polypeptide can be obtained by introducing mutation into DNA encoding an inhibitory substance binding type polypeptide according to the above-mentioned method.

The cloned DNA can be used as is, or after digestion with a restriction endonuclease or addition of a linker as desired, depending on the purpose of its use. The DNA may have the translation initiation codon ATG at the 5' end thereof, and the translation stop codon TAA, TGA or TAG at the 3' end thereof. These translation initiation codons and translation stop codons can be added by using a suitable synthetic DNA adaptor.

The protein or peptide can be produced by transforming a host with an expression vector containing a DNA encoding the above-mentioned TLR4 or a partial peptide thereof and cultivating the obtained transformant.

An expression vector containing a DNA encoding TLR4 or a partial peptide thereof can be produced, for example, by cleaving out an object DNA fragment from the DNA encoding TLR4 and connecting the DNA fragment with the downstream of a promoter in a suitable expression vector.

Useful expression vectors include plasmids derived from *E. coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); bacteriophages such as λ phage; animal viruses such as retrovirus, vaccinia virus and baculovirus; pA1-11, pXT1, pRc/CMV, pRc/RSV, pcDNAI/Neo and the like.

The promoter may be any promoter appropriate for the host used to express the gene.

For example, when an animal cell is used as the host, the SRα promoter, the SV40 promoter, the LTR promoter, the CMV (cytomegalovirus) promoter, the HSV-TK promoter and the like can be mentioned. Of these promoters, the CMV promoter, the SRα promoter and the like are preferably used.

When the host is a bacterium of the genus *Escherichia*, the trp promoter, the lac promoter, the recA promoter, the $\lambda P_L$ promoter, the lpp promoter, the T7 promoter and the like are preferred.

When the host is a bacterium of the genus *Bacillus*, the SPO1 promoter, the SPO2 promoter, the penP promoter and the like are preferred.

When the host is yeast, the PHO5 promoter, the PGK promoter, the GAP promoter, the ADH promoter and the like are preferred.

When the host is an insect cell, the polyhedrin promoter, the P10 promoter and the like are preferred.

Useful expression vectors include, in addition to the above, expression vectors that optionally comprise an enhancer, a splicing signal, a polyA addition signal, a selection marker, an SV40 replication origin (hereinafter also abbreviated as SV40ori), and the like. As examples of the selection markers, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance), and the like can be mentioned. In particular, when a dhfr gene-defective Chinese hamster ovary cell is used and the dhfr gene is used as the selection marker, a target gene can also be selected using a thymidine-free medium.

In addition, where necessary, a base sequence (single codon) encoding a signal sequence suitable for the host may be added to the 5' end side of DNA encoding TLR4 or a partial peptide thereof, or may be substituted by a native signal sequence (or prepro sequence). Useful signal sequences include a PhoA signal sequence, an OmpA signal sequence and the like when the host is a bacterium of the genus *Escherichia*; an α-amylase signal sequence, a subtilisin signal sequence and the like when the host is a bacterium of the genus *Bacillus*; an MFα signal sequence, an SUC2 signal sequence and the like when the host is yeast; and an insulin signal sequence, an α-interferon signal sequence, an antibody molecule signal sequence and the like when the host is an animal cell.

As useful examples of the host, a bacterium of the genus *Escherichia*, a bacterium of the genus *Bacillus*, yeast, an insect cell, an insect, an animal cell, and the like can be mentioned.

As useful examples of the bacterium of the genus *Escherichia, Escherichia coli* K12 DH1 (Proc. Natl. Acad. Sci. USA, vol. 60, 160 (1968)), JM103 (Nucleic Acids Research, vol. 9, 309 (1981), JA221 (Journal of Molecular Biology, vol. 120, 517 (1978)), HB101 (Journal of Molecular Biology, vol. 41, 459 (1969)), C600 (Genetics, vol. 39, 440 (1954)) and the like can be mentioned.

As useful examples of the bacterium of the genus *Bacillus, Bacillus subtilis* MI114 (Gene, Vol. 24, 255 (1983)), 207-21 (Journal of Biochemistry, Vol. 95, 87 (1984)) and the like can be mentioned.

As useful examples of the yeast, *Saccharomyces cerevisiae* AH22, AH22R$^-$, NA87-11A, DKD-5D and 20B-12, *Schizosaccharomyces pombe* NCYC1913 and NCYC2036, *Pichia pastoris* KM71 and the like can be mentioned.

As useful examples of the insect cell, *Spodoptera frugiperda* cell (Sf cell), MG1 cell derived from the mid-intestine of *Trichoplusia ni*, High Five™ cell derived from an egg of *Trichoplusia ni*, cell derived from *Mamestra brassicae*, cell derived from *Estigmena acrea*, and the like can be mentioned when the virus is AcNPV. When the virus is BmNPV, *Bombyx mori* N cell (BmN cell) and the like can be used. As useful examples of the Sf cell, Sf9 cell (ATCC CRL1711), Sf21 cell (both in Vaughn, J. L. et al., In Vivo, 13, 213-217 (1977)), and the like can be mentioned.

As useful examples of the insect, a larva of *Bombyx mori* (Maeda et al., Nature, Vol. 315, 592 (1985)), and the like can be mentioned.

As useful examples of the animal cell, monkey cell COS-7, Vero, Chinese hamster ovary cell (hereinafter abbreviated as CHO cell), dhfr gene-defective Chinese hamster ovary cell (hereinafter abbreviated as CHO(dhfr$^-$) cell), mouse L cell, mouse AtT-20, mouse myeloma cell, rat GH3 cell, human FL cell, HEK293 cell, HeLa cell and the like can be mentioned.

Transformation can be performed according to the choice of host by a commonly known method.

A bacterium of the genus *Escherichia* can be transformed, for example, in accordance with a method described in Proc. Natl. Acad. Sci. USA, Vol. 69, 2110 (1972), Gene, Vol. 17, 107 (1982) and the like.

A bacterium of the genus *Bacillus* can be transformed, for example, according to a method described in Molecular & General Genetics, Vol. 168, 111 (1979) and the like.

Yeast can be transformed, for example, in accordance with a method described in Methods in Enzymology, Vol. 194, 182-187 (1991), Proc. Natl. Acad. Sci. USA, Vol. 75, 1929 (1978) and the like.

An insect cell or insect can be transformed, for example, according to a method described in Bio/Technology, 6, 47-55 (1988) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, Vol. 52, 456 (1973).

Transformation can be performed according to the choice of host by a commonly known method.

When a transformant whose host is a bacterium of the genus *Escherichia* or a bacterium of the genus *Bacillus* is cultured, the culture medium used is preferably a liquid medium, in which a carbon source, a nitrogen source, an inorganic substance and others necessary for the growth of the transformant are preferably contained. Here, as examples of the carbon source, glucose, dextrin, soluble starch, sucrose and the like can be mentioned; as examples of the nitrogen source, inorganic or organic substances such as an ammonium salt, a nitrate salt, corn steep liquor, peptone, casein, meat extract, soybean cake, and potato extract can be mentioned; as examples of the inorganic substance, calcium chloride, sodium dihydrogen phosphate, magnesium chloride and the like can be mentioned. In addition, yeast extract, vitamins, a growth promoting factor and the like may be added to the medium. The pH of the medium is preferably about 5 to 8.

As an example of the medium used to culture a bacterium of the genus *Escherichia*, an M9 medium comprising glucose and casamino acid [Miller, Journal of Experiments in Molecular Genetics, 431-433, Cold Spring Harbor Laboratory, New York, 1972] is preferable. As required, in order to increase promoter efficiency, a chemical agent, for example, 3β-indolylacrylic acid, may be added to the medium.

When the host is a bacterium of the genus *Escherichia*, cultivation is normally performed at about 15 to 43° C. for about 3 to 24 hours, and the culture may be aerated or agitated as necessary.

When the host is a bacterium of the genus *Bacillus*, cultivation is normally performed at about 30 to 40° C. for about 6 to 24 hours, and the culture may be aerated or agitated as necessary.

When a transformant whose host is yeast is cultured, as examples of the medium, Burkholder's minimal medium [Proc. Natl. Acad. Sci. USA, Vol. 77, 4505 (1980)] and an SD medium supplemented with 0.5% casamino acid [Proc. Natl. Acad. Sci. USA, Vol. 81, 5330 (1984)] can be mentioned. The pH of the medium is preferably about 5 to 8. Cultivation is normally performed at about 20° C. to 35° C. for about 24 to 72 hours, and the culture may be aerated or agitated as necessary.

When a transformant whose host is an insect cell or insect is cultured, as the medium, Grace's Insect Medium (Nature, 195, 788 (1962)) supplemented with inactivated 10% bovine serum and other additives as appropriate and the like are used. The pH of the medium is preferably about 6.2 to 6.4. Cultivation is normally performed at about 27° C. for about 3 to 5 days, and the culture may be aerated or agitated as necessary.

Useful medium for cultivating a transformant whose host is an animal cell include, for example, MEM medium supplemented with about 5 to 20% fetal bovine serum [Science, Vol. 122, 501 (1952)], DMEM medium [Virology, Vol. 8, 396 (1959)], RPMI 1640 medium [The Journal of the American Medical Association, Vol. 199, 519 (1967)], 199 medium [Proceeding of the Society for the Biological Medicine, Vol. 73, 1 (1950)] and the like. The medium's pH is preferably about 6 to 8. Cultivation is normally performed at about 30 to 40° C. for about 15 to 60 hours, and the culture may be aerated or agitated as necessary.

Thus, the TLR4 or a partial peptide thereof can be produced in or outside the cells of the transformant.

The TLR4 or a partial peptide thereof can be separated and purified from the culture obtained by cultivating the aforementioned transformant according to a method known per se.

For example, when the TLR4 or a partial peptide thereof is extracted from cultivated bacteria or cells, a method is used as appropriate wherein the bacteria or cells are recovered from the culture by a known means, suspended in an appropriate buffer solution, and disrupted by means of sonication, lysozyme and/or freeze-thawing and the like, after which a crude extract of soluble protein is obtained by centrifugation or filtration. The buffer solution may contain a protein denaturant such as urea or guanidine hydrochloride and a surfactant such as Triton X-100™.

Isolation and purification of the TLR4 or a partial peptide thereof contained in the thus-obtained soluble fraction can be conducted according to a method know per se. Useful methods include methods based on solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography; methods based on differences in hydrophobicity, such as reverse phase high performance liquid chromatography; methods based on differences in isoelectric point, such as isoelectric focusing; and the like. These methods can be combined as appropriate.

When the thus-obtained TLR4 or a partial peptide thereof is a free form, the free form can be converted to a salt by a method known per se or a method based thereon; when the protein or the peptide is obtained as a salt, the salt can be converted to a free form or another salt by a method known per se or a method based thereon.

Note that the TLR4 or a partial peptide thereof produced by the transformant can be optionally modified or partially deprived of a polypeptide by allowing an appropriate protein-modifying enzyme to act thereon before the purification or after the purification. As the protein-modifying enzyme used, for example, trypsin, chymotrypsin, arginyl endopeptidase, protein kinase, glycosidase and the like are used.

The presence of the thus-obtained TLR4 or a partial peptide thereof can be confirmed by an enzyme immunoassay, Western blotting and the like using a specific antibody.

Furthermore, the TLR4 or a partial peptide thereof can also be synthesized by in vitro translation using a cell-free protein translation system that comprises a rabbit reticulocyte lysate, wheat germ lysate, *Escherichia coli* lysate and the like, with RNA corresponding to the above-described DNA that encodes TLR4 or a partial peptide thereof as the template. Alternatively, the transmembrane enzyme or a partial peptide thereof can be synthesized using a cell-free transcription/translation system containing RNA polymerase, with the DNA that encodes the transmembrane enzyme or a partial peptide thereof as the template. As the cell-free protein (transcription/) translation system, commercially available ones can be used, a method known per se, and specifically, an *Escherichia coli* extract can also be prepared by the method described in Pratt J. M. et al., *Transcription and Translation*, 179-209, Hames B. D. & Higgins S. J. eds., IRL Press, Oxford (1984) and the like. As the commercially available cell lysates, as those derived from *Escherichia coli, E. coli* S30 extract system (manufactured by Promega), RTS 500 Rapid Translation System (manufactured by Roche) and the like can be mentioned, as those derived from rabbit reticulocyte, Rabbit Reticulocyte Lysate System (manufactured by Promega) and the like can be mentioned, and as those derived from wheat germ, PROTEIOS™ (manufactured by TOYOBO) and the like can be mentioned. Of these, ones using a wheat germ lysate are preferable. As the production method of wheat germ lysate, for example, the methods described in Johnston F. B. et al., *Nature*, 179: 160-161 (1957) or Erickson A. H. et al., *Meth. Enzymol.*, 96: 38-50 (1996) and the like can be used.

As the system or apparatus for protein synthesis, batch method (Pratt, J. M. et al. (1984), mentioned above), continuous cell-free protein synthesis system (Spirin A. S. et al., *Science*, 242: 1162-1164 (1988)) wherein amino acid, energy source and the like are continuously supplied to the reaction system, dialysis (Kikawa et al., The 21st Annual Meeting of the Molecule Biology Society of Japan, WID6), or overlay method (manual of PROTEIOS™ Wheat germ cell-free protein synthesis core kit: manufactured by TOYOBO) and the like can be mentioned. Moreover, a method (JP-A-2000-333673) wherein template RNA, amino acid, energy source and the like are supplied to a synthesis reaction system as necessary and a synthesized substance and decomposed product are discharged as necessary, and the like can be used.

The screening method of the present invention is characterized by measurement, using an inhibitory substance binding type polypeptide obtained by any of the above-mentioned methods, of the binding of a test compound to an intracellular region of TLR4 of the polypeptide and, when the polypeptide retains a signal transduction activity, a signal transduction activity in the presence of a test compound.

To be specific, for example, the binding of a test compound to an intracellular region of TLR4 can be determined by preparing a solid phased (e.g., microplate etc.) inhibitory substance binding type polypeptide, adding a solution containing a labeled test compound to the solid phase, incubating the mixture for a predetermined time, removing the solution, and measuring the amount of label absorbed to the solid phase. Alternatively, when the inhibitory substance binding type polypeptide is a fusion polypeptide having a suitable tag (e.g., GST tag, His tag, MBP tag), the binding of a test compound to an intracellular region of TLR4 can also be determined by reacting the polypeptide with a labeled test compound in the solution, pulling down the polypeptide using a carrier (e.g., beads solid phased with glutathione, metal chelate, maltose etc. and the like) containing a substance that specifically binds to the tag sequence, and measuring the amount of label absorbed to the solid phase. As the labeling agent, for example, a radioisotope, an enzyme, a fluorescent substance, a luminescent substance and the like can be used. As the radioisotope, for example, [$^{125}$I], [$^{131}$I], [$^{3}$H], [$^{14}$C] and the like can be used. The above-described enzyme is preferably stable and has a high specific activity and, for example, β-galactosidase, β-glucosidase, alkaline phosphatase, peroxidase, malate dehydrogenase and the like can be used. As the fluorescent substance, for example, fluorescamine, fluorescein isothiocyanate and the like can be used. As the luminescent substance, for example, luminol, luminol derivative, luciferin, lucigenin and the like can be used.

Alternatively, for the binding of an inhibiting substance binding type polypeptide and a test compound, the presence or absence of the binding of a test compound to the immobilized inhibiting substance binding type polypeptide can be determined, for example, using surface plasmon resonance (SPR) and the change in the resonance angle as an index, wherein the inhibiting substance binding peptide is immobilized onto the surface of a commercially available sensorchip (e.g., manufactured by Biacore) according to a conventional method, the test compound is contacted therewith, and then the sensorchip is illuminated with a light of a particular wavelength from a particular angle. Alternatively, the binding of an inhibiting substance binding type polypeptide and a test compound can also be measured by detecting the appearance of a peak corresponding to the test substance by a method wherein the inhibiting substance binding type polypeptide is immobilized onto the surface of a protein chip adaptable to a mass spectrometer, a test substance is contacted therewith, and then ionization method such as MALDI-MS, ESI-MS, FAB-MS and the like and mass spectrometer (e.g., double-focusing mass spectrometer, quadrupole mass spectrometer, time-of-flight mass spectrometer, Fourier transformation mass spectrometer, ion cyclotron mass spectrometer and the like) are combined. However, the methods for measuring are not limited thereto, and any other known methods are also available.

Binding of a test compound to the target binding site in an intracellular region of TLR4 in an inhibitory substance binding type polypeptide can be confirmed by measuring the binding activity of the test compound in the same manner as above and using an inhibitory substance non-binding type polypeptide instead of the inhibitory substance binding type polypeptide.

A substance that binds to the inhibitory substance binding type polypeptide but does not bind to the inhibitory substance non-binding type polypeptide as a result of the measurement can be selected as a compound that binds to the target binding site in the intracellular region of TLR4.

The TLR4 signal transduction inhibitory activity of a test compound can be determined by examining, in the presence or absence of the test compound, the TLR4 signal transduction by a cell that expresses TLR4. To be specific, it can be determined by measuring the expression of inflammatory cytokine (e.g., TNFα, IL-1, IL-6 and the like) or variation of expression of IFN-α, IFN-β or interferon-induced gene at the RNA level by Northern blot, RT-PCR and the like, or at the protein level by using an antibody of each gene product. Examples of the cell that expresses TLR4 include mammalian cell that expresses inherent TLR4, or a transformed cell containing DNA encoding TLR4 or a partial peptide thereof (including transient expression), preferably a mammalian cell, more preferably a human cell, mentioned above in respect to the production of TLR4 or a partial peptide thereof.

For example, when the expression level of the above-mentioned gene decreases by not less than 20% in the presence of a test compound, the test compound can be selected as a TLR4 signal transduction inhibitory substance.

The expression of inflammatory cytokine by TLR4 signal is induced via activation of NF-κB, which activates transcription of an inflammatory cytokine gene having, in a promoter region, a cis-element specific to said transcription factor. In addition, the expression of IFN-β and an interferon-induced gene by TLR4 signal is induced via activation of IRF3, which activates transcription of IFN-β and the interferon-induced gene having, in a promoter region, a cis-element specific to said transcription factor. Thus, in a more preferred embodiment, the TLR4 signal transduction inhibitory activity of a compound can be determined by culturing, in the presence or absence of a test compound, a cell that expresses an inhibitory substance binding type polypeptide and contains a gene, preferably a reporter gene, under regulation of a promoter containing an NF-κB or IRF3 binding sequence, for a given time, and measuring the expression level of the gene.

Examples of the cell that expresses an inhibitory substance binding type polypeptide include those similar to the cells mentioned above. Since TLR4 signal is activated by LPS (TLR4 ligand), the inhibitory substance binding type polypeptide to be used preferably contains an LPS binding region in an extracellular region of TLR4, so that it can respond to LPS stimulation. In addition, the polypeptide desirably contains a transmembrane region and a signal peptide suitable for the cell, so that the polypeptide can correctly bind to the membrane. As the NF-κB binding sequence, GGGRNNYYCC (SEQ ID NO: 3) can be mentioned, and as the IRF3 bond sequence, GAAASSGAAANY (SEQ ID NO: 4) can be mentioned. A sequence other than the above-mentioned consensus sequence may also be used as long as such transcription factors bind thereto in a promoter region of a gene known to be under regulation of expression by the transcription factors. The promoter to be used is not particularly limited as long as it is functional in a host cell to be used, and any of the above-mentioned promoters is exemplified according to the host cell. When an animal cell is used as the host cell, the promoter to be used may be a promoter derived from an NF-κB binding sequence or IRF3 binding sequence to be used. As the reporter gene, luciferase gene, GFP gene, EGFP gene, peroxidase gene, alkaliphosphatase gene and the like can be mentioned, though not limited thereto. A gene under control of a promoter containing an NF-κB or IRF3 binding sequence can be inserted into any of the vectors mentioned above according to the host cell, and introduced into the host cell by the above-mentioned suitable gene transfer method.

The above-mentioned cell can be cultured in the same manner as above in the above-mentioned various media, phosphate buffered saline and the like according to the host cell. The baseline of TLR4 signal (expression level of reporter gene in the absence of a test compound) can be increased by adding, besides a test compound, LPS when an inhibitory binding type polypeptide contains a ligand binding region, to a medium or buffer. After completion of culture, the expression level of the reporter gene is measured. As the measurement method, a method known per se for each reporter gene can be used.

For example, when the level of expression of the reporter gene decreased by not less than 20% in the presence of the test compound, the test compound can be selected as a TLR4 signal transduction inhibitory substance.

In a particularly preferable embodiment of the screening method of the present invention, the above-mentioned reporter assay is performed using a cell that expresses an inhibitory substance binding type polypeptide (sample 1), and a cell that expresses an inhibitory substance non-binding type polypeptide wherein the binding site of the objective TLR4 signal inhibitory substance has been mutated (sample 2). As a result, the presence or absence of binding of a test compound to a target binding site, as well as the TLR4 signal transduction inhibitory activity of the test compound can be measured simultaneously. That is, in sample 2, since a TLR4 signal inhibitory substance that binds to the target site does not bind to an inhibitory substance non-binding type polypeptide, it does not inhibit TLR4 signal, and the expression level of a reporter gene does not decrease. According to this method, therefore, culture of the cell in the absence of a test compound and measurement of the expression level of the reporter gene are not necessary.

For example, when the expression level of the reporter gene in sample 1 decreased by not less than 20% in comparison with that in sample 2, the test compound can be selected as a TLR4 signal transduction inhibitory substance.

Accordingly, the present invention also provides a kit for screening for a TLR4 signal transduction inhibitory substance, comprising, as elements, a cell that expresses the above-mentioned inhibitory substance binding type polypeptide, and a cell that expresses an inhibitory substance non-binding type polypeptide wherein the binding site of the objective TLR4 signal inhibitory substance has been mutated. The kit may further contain, as elements, a medium and a container for cell culture, a reagent for detection of the expression of a reporter gene and the like.

As obtained by screening in the present invention, a substance that binds to an intracellular region of TLR4, and inhibits signal transduction of TLR4 (hereinafter to be abbreviated as the TLR4 signal transduction inhibitory substance of the present invention) is useful, for example, as a nitric oxide (NO) production suppressing agent, an inflammatory cytokine production suppressing agent such as TNF-α, IL-1, IL-6 and the like, a TLR signal inhibitor (particularly, a TLR4 signal inhibitor) and the like for mammals (e.g., rat, mouse, guinea pig, monkey, bovine, dog, swine, human etc.).

In addition, the TLR4 signal transduction inhibitory substance of the present invention is useful as an agent for the prophylaxis or treatment of sepsis including severe sepsis to a mammal (e.g., rat, mouse, guinea pig, monkey, cattle, dog, swine, human etc.), cardiac disease, autoimmune disease, inflammatory disease, central nervous system diseases, infectious disease, septic shock, immune dysfunction and the like, including, for example, septicemia, endotoxin shock, exotoxin shock, systemic inflammatory response syndrome (SIRS), compensatory anti-inflammatory response syndrome (CARS), burn, trauma, post-operative complications, cardiac deficiency, shock, hypotension, rheumatoid arthritis, osteoarthritis, gastritis, ulcerative colitis, peptic ulcer, stress-induced gastric ulcer, Crohn's disease, autoimmune disease, post-transplant tissue failure and rejection, postischemic re-perfusion failure, acute coronary microvascular embolism, shock-induced vascular embolism (disseminated intravascular coagulation (DIC) etc.), ischemic cerebral disorder, arteriosclerosis, pernicious anemia, Fanconi's anemia, drepanocythemia, pancreatitis, nephrose syndrome, nephritis, renal failure, insulin-dependent diabetes, insulin-independent diabetes, hepatic porphyria, alcoholism, Parkinson's disease, chronic leukemia, acute leukemia, tumor, myeloma, infantile and adult respiratory distress syndrome, pulmonary emphysema, dementia, Alzheimer's disease, multiple sclerosis, vitamin E deficiency, aging, sunburn, muscular dystrophy, myocarditis, cardiomyopathy, myocardial infarction, myocardial post infarction syndrome, osteoporosis, pneumonia, hepatitis, psoriasis, pain, cataract, influenza infection, malaria, human immunodeficiency virus (HIV) infection, radiation hazard, burn, in vitro fertilization efficiency, hypercalcemia, tonic spondylitis, osteopenia, bone Paget's disease, osteomalacia, fracture, acute bacterial meningitis, *Helicobacter pylori* infection, invasive staphylococcal infection, tuberculosis, systemic mycosis, herpes simplex virus infection, varicella-zoster virus infection, human papilloma virus infection, acute viral encephalitis, encephalitis, meningitis, immune dysfunction due to infections, asthma, atopic dermatitis, allergic rhinitis, reflux esophargitis, fever, hyper cholesteremia, hyperglycemia, hyperlipidemia, diabetic complication, diabetic renal disease, diabetic neuropathy, diabetic retinopathy, gout, gastric atony, hemorrhoid, systemic lupus erythematosus, spinal damage, insomnia, schizophrenia, epilepsy, cirrhosis, hepatic failure, instable angina, valvular disease, dialysis-induced thrombocytopenia or hypotonia, acute ischemic cerebral apoplexy, acute cerebral thrombosis, cancer metastasis, urinary bladder cancer, mammary cancer, cancer of the uterine cervix, colon cancer, gastric cancer, ovarian cancer, prostatic cancer, parvicellular pulmonary cancer, non-parvicellular pulmonary cancer, malignant melanoma, Hodgkin's disease, non-Hodgkin lymphoma, side effects caused by administration of anticancer agents or immunosuppressants and the like.

Furthermore, the TLR4 signal transduction inhibitory substance of the present invention is also useful as an agent for the prophylaxis or treatment of, for example, organ disorder in a mammal (e.g., rat, mouse, guinea pig, monkey, bovine, dog, swine, human etc.) and the like. Here, the organ refers to various organs of central nervous system, circulatory, respiratory, osseous-articular system, circulatory system or glandurinary system. More specifically, the TLR4 signal transduction inhibitory substance of the present invention is useful as an agent for the prophylaxis or treatment of (1) central nervous system diseases [(i) neurodegenerative disease (e.g., senile dementia, Alzheimer's disease, Down's syndrome, Parkinson's disease, Creutzfeldt-Jakob disease, amyotrophic spinal lateral sclerosis, diabetic neuropathy etc.), (ii) neuropathy in cerebrovascular diseases (e.g. impairment of cerebral blood flow based on cerebral infarction, cerebral hemorrhage, cerebral sclerosis, etc.), brain trauma, spiral cord injury, cerebritis sequela and cerebral palsy, (iii) dysmnesia (e.g. senile dementia, amnesia, etc.) and the like], particularly Alzheimer's disease, (2) circulatory system diseases [(i) coronary artery syndrome such as acute myocardial infarction and unstable angina pectoris, (ii) peripheral obstruction, (iii) restenosis after coronary intervention (percutaneous transluminal coronary angioplasty (PTCA), atherectomy (DCA), stenting etc.), (iv) restenosis after coronary bypass surgery, (v) restenosis after other peripheral arterial interventions (angioplasty, atherectomy, stenting etc.) and bypass surgery, (vi) ischemic heart disease such as myocardial infarction and angina pectoris, (vii) intermittent claudication, (viii) stroke (cerebral infarction, cerebral embolus, cerebral hemorrhage etc.), (ix) lacunar infarct, (x) cerebrovascular dementia, (xi) arteriosclerosis (e.g., atherosclerosis etc.) and diseases caused thereby (e.g., ischemic heart disease such as myocardial infarction, cerebrovascular disorder such as cerebral infarction-stroke, etc.), (xii) cardiac failure, (xiii) arrhythmia, (xiv) progression of focus of arteriosclerosis, (xv) thrombogenesis, (xvi) hypotension, (xvii)

shock, (xviii) shock-induced vascular embolism (disseminated intravascular coagulation (DIC) etc.)], particularly arteriosclerosis, (3) respiratory system diseases [respiratory distress syndrome, respiratory failure, emphysema, pneumonia, bronchitis, bronchiolitis and the like], (4) diseases of bone and joint system [arthritis rheumatoides, osteoporosis, osteomalacia, osteopenia, Paget's disease of bone and the like], particularly arthritis rheumatoides, (5) diseases of digestive-liver, biliary tract and pancreas system [ulcerative colitis, gastritis, digestive ulcer, cirrhosis, hepatic failure, hepatitis, cholecystitis, pancreatitis and the like], particularly ulcerative colitis, (6) diseases of renal and urinary system [nephritis, kidney failure, cystitis and the like], which are caused by the change of TLR signal, or a combination of these diseases (multiple organ failure etc.) and the like. Furthermore, the TLR4 signal transduction inhibitory substance of the present invention is useful as an agent for the prophylaxis or treatment of infectious diseases caused by the change of TLR4 signal, particularly sepsis (severe sepsis) accompanied by organ disorder.

Furthermore, the TLR4 signal transduction inhibitory substance of the present invention is also useful as an agent for the prophylaxis or treatment of infectious diseases such as organ disorder, severe sepsis and the like, central nervous system diseases such as Alzheimer's disease and the like, circulatory diseases such as arteriosclerosis and the like, osseous-articular system diseases such as chronic rheumatoid arthritis and the like, digestive system diseases such as ulcerative colitis etc. and the like.

The TLR4 signal transduction inhibitory substance of the present invention can be used concurrently with other drugs. As the combination drugs, for example, antibacterial agents, antifungal agents, non-steroidal antiinflammatory drugs, steroids, anticoagulants, antithrombotic drugs, thrombolytic drugs, immunomodulators, antiprotozoals, antitussive and expectorant drugs, sedatives, anesthetics, antinarcotics, antiulcer drugs, hyperlipidemia treating agents, therapeutic agents for arteriosclerosis, HDL increasing agents, unstable plaque stabilizing agents, myocardial protecting agent, hypothyroidism treating agent, nephrotic syndrome treating agent, chronic renal failure treating agent, diuretics, hypertension treating agents, cardiac failure treating agents, muscle relaxants, anticonvulsants, cardiacs, vasodilators, vasoconstrictors, antiarrhythmics, antidiabetic drugs, hypertensors, tranquilizers, antipsychotics, therapeutic agents for Alzheimer's diseases, anti-Parkinson drugs, therapeutic agents for amyotrophic spinal lateral sclerosis, neurotrophic factors, antidepressants, therapeutic agents for schizophrenia, antitumor drugs, vitamins, vitamin derivatives, therapeutic agents for arthritis, antirheumatics, antiallergic drugs, antiasthmatics, therapeutic agents for atopic dermatitis, therapeutic agents for allergic rhinitis, therapeutic agents for pollakisuria/anischuria, protease drugs, protease inhibitors, anti-SIDS drugs, anti-sepsis drugs, anti-septic shock drugs, endotoxin-antagonists or -antibodies, signal transduction inhibitors, inhibitors of inflammatory mediator activity, antibodies to inhibit inflammatory mediator activity, inhibitors of inflammatory mediator production, inhibitors of anti-inflammatory mediator activity, antibodies to inhibit anti-inflammatory mediator activity, inhibitors of anti-inflammatory mediator production, α1-adrenergic stimulating agents and the like can be mentioned. Of these, antibacterial agents, antifungal agents, non-steroidal antiinflammatory drugs, steroids, anticoagulants and the like are preferable. Specific examples thereof include the following.

(1) Antibacterial Agents (i) Sulfa Drugs sulfamethizole, sulfisoxazole, sulfamonomethoxine, sulfamethizole, salazosulfapyridine, silver sulfadiazine and the like.

(ii) Quinoline Antibacterial Agents nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like.

(iii) Antiphthisics isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.

(iv) Antiacidfast Bacterium Drugs diaphenylsulfone, rifampicin and the like.

(v) Antiviral Drugs idoxuridine, acyclovir, vidarabine, ganciclovir and the like.

(vi) Anti-HIV Agents zidovudine, didanosine, zalcitabine, indinavir sulfate ethanolate, ritonavir and the like.

(vii) Antispirocheteles (viii) Antibiotics tetracycline hydrochloride, ampicillin, piperacillin, gentamicin, dibekacin, kanendomycin, lividomycin, tobramycin, amikacin, fradiomycin, sisomycin, tetracycline, oxytetracycline, rolitetracycline, doxycycline, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [Journal of Antibiotics, 38, 877-885 (1985)] and the like.

(2) Antifungal Agents (i) polyethylene antibiotics (e.g., amphotericin B, nystatin, trichomycin)

(ii) griseofulvin, pyrrolnitrin and the like.

(iii) cytosine metabolism antagonists (e.g., flucytosine)

(iv) imidazole derivatives (e.g., econazole, clotrimazole, miconazole nitrate, bifonazole, croconazole)

(v) triazole derivatives (e.g. fluconazole, itraconazole, azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone]

(vi) thiocarbamic acid derivatives (e.g. trinaphthol)

(vii) echinocandin derivatives (e.g., caspofungin, micafungin, anidulafungin) and the like.

(3) Non-Steroidal Antiinflammatory Drugs acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesylate, camostat mesylate, urinastatin, colchicine, probenecid, sulfinpyrazone, benzbromarone, allopurinol, gold sodium thiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof, and the like.

(4) Steroids dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclometasone propionate, estriol and the like.

(5) Anticoagulants heparin sodium, sodium citrate, activated protein C, tissue factor pathway inhibitor, antithrombin III, dalteparin sodium, warfarin potassium, argatroban, gabexate, sodium citrate and the like.

(6) Antithrombotic Drugs ozagrel sodium, ethyl icosapentate, beraprost sodium, alprostadil, ticlopidine hydrochloride, pentoxifylline, dipyridamole and the like.

(7) Thrombolytic Drugs tisokinase, urokinase, streptokinase and the like.

(8) Immunomodulators cyclosporin, tacrolimus, gusperimus, azathioprine, antilymphocyte serum, dried sulfonated immunoglobulin, erythropoietin, colony-stimulating factor, interleukin, interferon and the like.

(9) Antiprotozoals metronidazole, tinidazole, diethylcarbamazine citrate, quinine hydrochloride, quinine sulfate and the like.

(10) Antitussive and Expectorant Drugs ephedrine hydrochloride, noscapine hydrochloride, codeine phosphate, dihydrocodeine phosphate, isoproterenol hydrochloride, methylephedrine hydrochloride, noscapine hydrochloride, alloclamide, chlophedianol, picoperidamine, chloperastine, protokylol, isoproterenol, salbutamol, terbutaline, oximetebanol, morphine hydrochloride, dextromethorphan hydrogen bromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(11) Sedatives chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(12) Anesthetics (12-1) Local Anesthetics cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(12-2) General Anesthetics (A) inhalation anesthetics (e.g., ether, halothane, nitrous oxide, isoflurane, enflurane), (B) intravenous anesthetics (e.g., ketamine hydrochloride, droperidol, thiopental sodium, thiamylal sodium, pentobarbital) and the like.

(13) Antinarcotics levallorphan, nalorphine, naloxone or a salt thereof and the like.

(14) Antiulcer Drugs metoclopromide, histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(15) Hyperlipidemia Treating Agents

HMG-CoA reductase inhibitors (e.g., fluvastatin, cerivastatin, atorvastatin etc.), fibrates (e.g., simfibrate, clofibrate aluminum, clinofibrate, fenofibrate etc.), adsorbents for bile acid (e.g., cholestyramide etc.), nicotinic acid formulations (e.g., nicomol, niceritrol, tocopherol nicotinate etc.), probucol and a derivative thereof, polyvalent unsaturated fatty acid derivatives (e.g., ethyl icosapentate, polyene phosphatidylcholine, melinamide etc.), vegetable sterols (e.g., gammaoryzanol, soysterol etc.), elastases, sodium dextran sulfate, squalene synthetase inhibitor, squalene epoxidase inhibitor, CETP inhibitor, ethyl 2-chloro-3-[4-(2-methyl-2-phenylpropoxy)phenyl]propionate [Chem. Pharm. Bull., 38, 2792, 2796 (1990)], LDL receptor enhancing drug, cholesterol absorption inhibitor (Ezetimibe etc.), MTP inhibitor, ileal bile acid transporter inhibitor, SCAP ligand, FXR ligand and the like.

(16) Therapeutic Agents for Arteriosclerosis

MMP inhibitor, chymase inhibitor, ACAT inhibitor (Avasimibe, Eflucimibe etc.), apoAI Milano and an analogue thereof, scavenger receptor inhibitor, 15-lipoxygenase inhibitor, phospholipase A2 inhibitor, ABCA1 activator, LXR ligand, sphingomyelinase inhibitor, paraoxonase activator, estrogen receptor agonist and the like.

(17) HDL Increasing Agents squalene synthetase inhibitors, CETP inhibitors, LPL activators and the like.

(18) Unstable Plaque Stabilizing Agents

MMP inhibitors, chymase inhibitors, ACAT inhibitors, lipid-rich plaque regressing agents and the like.

(19) Myocardial Protecting Agents cardiac ATP-K oral formulation, encloserine antagonist, urotensin antagonist and the like.

(20) Hypothyroidism Treating Agents dried thyroid gland (thyreoid), levothyroxine sodium (thyradin S), liothyronidin sodium (thyronine, thyromin) and the like.

(21) Nephrotic Syndrome Treating Agents prednisolone (Predonine), prednisolone succinate sodium (Predonine), methylprednisolone succinate sodium (Solu medrol), betamethasone (rinderon) and the like.

(22) Chronic Renal Failure Treating Agents diuretics [e.g., furosemide (lasix), bumetamide (lunetron), azosemide (diart)], hypotensive agent (e.g., ACE inhibitor, enalapril maleate (renivase) and Ca antagonist (manidipine), α-receptor blocker, AII antagonist (candesartan)] and the like.

(23) Diuretics thiazide diuretics (benzylhydro-chlorothiazide, cyclopenthiazide, ethiazide, hydrochlorothiazide, hydroflumethiazide, methyclothiazide, penfluthiazide, polythiazide, trichloromethiazide etc.), loop diuretics (clortharidone, clofenamide, indapamide, mefruside, meticrane, sotolazone, tripamide, quinethazone, metolazone, furosemide etc.), potassium retaining diuretics (spironolacton, triamterene etc.).

(24) Hypertension Treating Agents (i) Sympathetic Nerve Suppressants $α_2$ stimulants (e.g., clonidine, guanabenz, guanfacine, methyldopa etc.), ganglionic blocking agents (e.g., hexamethonium, trimethaphan etc.), presynaptic blockers (e.g., alseroxylon, dimethylaminoreserpinate, rescinamine, reserpine, syrosingopine etc.), neuron blockers (e.g., betanidine, guanethidine etc.), $α_1$ blockers (e.g., bunazosin, doxazocin, prazosin, terazosin, urapidil etc.), β blockers (e.g., propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol etc.).
(ii) Vasodilators
calcium channel antagonists (e.g., manidipine, nicardipine, nilvadipine, nisoldipine, nitrendipine, benidipine, amlodipine, aranidipine etc.), phthalazine derivatives (e.g., budralazine, cadralazine, ecarazine, hydralazine, todralazine etc.) and the like.
(iii) ACE Inhibitors
alacepril, captopril, cilazapril, delapril, enalapril, lisinopril, temocapril, trandolapril, quinapril, imidapril, benazepril, berindopril and the like.
(iv) AII Antagonists
losartan, candesartan, valsartan, termisartan, irbesartan, forasartan and the like.
(v) Diuretics (e.g., Diuretics Described Above)
(25) Cardiac Failure Treating Agents
cardiotonic agents (e.g., digitoxin, digoxin, methyldigoxin, lanatoside C, proscillaridine etc.), $\alpha,\beta$-stimulants (e.g., epinephrine, norepinephrine, isoproterenol, dopamine, docarpamine, dobutamine, denopamine etc.), phosphodiesterase inhibitors (e.g., aminone, milrinone, olprinone hydrochloride etc.), calcium channel sensitivity promoters (e.g., pimobendan etc.), nitrate agents (e.g., nitroglycerin, isosorbide nitrate etc.), ACE inhibitors (e.g., ACE inhibitors described above), diuretics (e.g., diuretics described above), carperitide, ubidecarenone, vesnarinone, aminophylline and the like.
(26) Muscle Relaxants
pridinol, tubocurarine, pancuronium, tolperisone hydrochloride, chlorphenesin carbamate, baclofen, chlormezanone, mephenesin, chlorzoxazone, eperisone, tizanidine and the like.
(27) Anticonvulsants
phenyloin, ethosuximide, acetazolamide, chlordiazepoxide, trimethadione, carbamazepine, phenobarbital, primidone, sulthiame, sodium valproate, clonazepam, diazepam, nitrazepam and the like.
(28) Cardiacs
trans-pi-oxocamphor, terephyllol, aminophyllin, etilefrine, dopamine, dobutamine, denopamine, aminophyllin, bencirin, aminone, pimobendan, ubidecarenone, digitoxin, digoxin, methyldigoxin, lanatoside C, G-strophanthin and the like.
(29) Vasodilators
oxyfedrine, diltiazem, tolazoline, hexobendine, bamethan, clonidine, methyldopa, guanabenz and the like.
(30) Vasoconstrictors
dopamine, dobutamine, denopamine and the like.
(31) Antiarrhythmics
(A) Na channel blockers (e.g., quinidine, procainamide, disopyramide, ajmaline, cibenzoline, lidocaine, diphenylhydantoin, mexiletine, propafenone, flecamide, pilsicamide, phenitoin etc.),
(B) β-blockers (e.g., propranolol, alprenolol, bufetolol, oxprenolol, atenolol, acebutolol, metoprolol, bisoprolol, pindolol, carteolol, arotinolol etc.),
(C) K channel blockers (e.g., amiodarone etc.),
(D) Ca channel blockers (e.g., verapamil, diltiazem etc.) and the like.
(32) Hypertensors
dopamine, dobutamine, denopamine, digitoxin, digoxin, methyldigoxin, lanatoside C, G-strophanthin and the like.
(33) Antidiabetic Drugs
sulfonylureas (e.g., tolbutamide, chlorpropamide, glyclopyramide, acetohexamide, tolazamide, glibenclamide, glybuzole etc.), biguanides (e.g., metformin hydrochloride, buformin hydrochloride etc.), $\alpha$-glucosidase inhibitors (e.g., voglibose, acarbose etc.), insulin sensitizers (e.g., pioglitazone, rosiglitazone, troglitazone etc.), insulin, glucagon, agents for treating diabetic complications (e.g., epalrestat etc.) and the like.
(34) Tranquilizers
diazepam, lorazepam, oxazepam, chlordiazepoxide, medazepam, oxazolam, cloxazolam, clotiazepam, bromazepam, etizolam, fludiazepam, hydroxyzine and the like.
(35) Antipsychotics
chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.
(36) Therapeutic Agents for Alzheimer's Diseases
(i) choline esterase inhibitors such as donepezil, rivastigmine, galanthamine, TAK-147 and the like.
(ii) cerebral function activators such as Idebenone, Memantine, vinpocetine and the like.
(37) Anti-Parkinson Drugs
L-dopa, Deprenyl, carbidopa+levodopa, Pergolide, Ropinirole, cabergoline, Pramipexol, Entacapone, Lazabemide and the like.
(38) Therapeutic Agents for Amyotrophic Spinal Lateral Sclerosis
riluzole, mecasermin, Gabapentin and the like.
(39) Antidepressants
imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.
(40) Therapeutic Agents for Schizophrenia
Olanzapine, risperidone, Quetiapine, Iloperidone and the like.
(41) Antitumor Drugs
6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulphan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestol, chlormadinone acetate, leuprorelin acetate, buserelin acetate and the like.
(42) Vitamins
(A) vitamin A: vitamin $A_1$, vitamin $A_2$ and retinol palmitate
(B) vitamin D: vitamin $D_1$, $D_2$, $D_3$, $D_4$ and $D_5$
(C) vitamin E: $\alpha$-tocopherol, $\beta$-tocopherol, $\gamma$-tocopherol, $\delta$-tocopherol, dl-$\alpha$-tocopherol nicotinate
(D) vitamin K: vitamin $K_1$, $K_2$, $K_3$ and $K_4$
(E) folic acid (vitamin M)
(F) vitamin B: vitamin $B_1$, vitamin $B_2$, vitamin $B_3$, vitamin $B_5$, vitamin $B_6$ and vitamin $B_{12}$
(G) biotin (vitamin H) and the like.
(43) Vitamin Derivatives
various derivatives of vitamins, for example, vitamin $D_3$ derivatives such as ascorbic acid, 5,6-trans-cholecalciferol, 2,5-hydroxycholecalciferol, 1-α-hydroxycholecalciferol and the like, vitamin $D_2$ derivatives such as 5,6-trans-ergocalciferol and the like.

(44) Antiallergic Drugs diphenhydramine, chlorpheniramine, tripelennamine, metodilamine, clemizole, diphenylpyraline, methoxyphenamine, sodium cromoglycate, tranilast, repirinast, amlexanox, ibudilast, ketotifen, terfenadine, mequitazine, azelastine, epinastine, ozagrel hydrochloride, pranlkast hydrate, seratrodast and the like.

(45) Antiasthmatics isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrogen bromide, ephedrine hydrochloride, iprotropium bromide, oxitropium bromide, flutropium bromide, theophyline, aminophyllin, sodium cromoglycate, tranilast, repirinast, anrexanone, ibudilast, ketotifen, terfenadine, mequitazine, azelastine, epinastine, ozagrel hydrochloride, pranlkast hydrate, seratrodast, dexamethasone, prednisolone, hydrocortisone, beclometasone dipropionate and the like.

(46) Therapeutic Agents for Atopic Dermatitis sodium cromoglycate and the like.

(47) Therapeutic Agents for Allergic Rhinitis sodium cromoglycate, chlorpheniramine maleate, alimemazine tartrate, clemastine fumarate, homochlorcyclizine hydrochloride, terfenadine, mequitazine and the like.

(48) Therapeutic Agents for Pollakisuria/Anischuria flavoxate hydrochloride and the like.

(49) Anti-Sepsis Drugs peptidic compounds such as rBPI-21 (bactericidal permeability increasing protein), BI-51017 (antithrombin III), SC-59735 (rTFPI), r-PAF acetylhydrase, LY-203638 (r-activated protein C), anti-TNF-α antibody, anti-CD14 antibody, CytoFab, alkaline phosphatase (LPS inactivator) and the like, and non-peptidic compounds such as JTE-607, E-5531, E-5564, S-5920, FR-167653, ONO-1714, ONO-5046 (sivelestat), GW-273629, RWJ-67657, GR-270773, NOX-100, GR-270773, NOX-100 and the like.

(50) Antiemetic phenothiazine derivative, 5-HT3 receptor antagonist and the like.

(51) Methhemoglobin Increase Preventive methylene blue, ascorbic acid and the like.

(52) Others hydroxycam, diaserine, megestrol acetate, nicerogolin, prostaglandins and the like.

A combined use of the TLR4 signal transduction inhibitory substance of the present invention and other drugs provides the following effects.

(1) The doses of the TLR4 signal transduction inhibitory substance of the present invention and a concomitant drug can be reduced from those of single administration thereof.

(2) A synergistic therapeutic effect can be achieved.

(3) A broad therapeutic effects can be achieved against various diseases developed in association with bacterial infection and the like.

(4) Side effects of the TLR4 signal transduction inhibitory substance of the present invention can be reduced.

For the combined use, the TLR4 signal transduction inhibitory substance of the present invention and a concomitant drug are free of any limitation on the timing of the administration. The TLR4 signal transduction inhibitory substance of the present invention or a pharmaceutical composition thereof and the concomitant drug or a pharmaceutical composition thereof may be simultaneously administered to the administration object, or may be administered with time difference. The dose of the concomitant drug follows a clinical dose and can be appropriately determined depending on the administration object, administration route, disease, combination and the like.

The administration mode of the concomitant drug is not particularly limited, and the TLR4 signal transduction inhibitory substance of the present invention and the concomitant drug only need to be combined on administration. Examples of such administration mode include the following (1) administration of a single preparation obtained by simultaneously processing the TLR4 signal transduction inhibitory substance of the present invention or a pharmaceutical composition thereof and the concomitant drug, (2) simultaneous administration of two kinds of preparations of the TLR4 signal transduction inhibitory substance of the present invention or a pharmaceutical composition thereof and the concomitant drug or a pharmaceutical composition thereof, which have been separately produced, by the same administration route, (3) administration of two kinds of preparations of the TLR4 signal transduction inhibitory substance of the present invention or a pharmaceutical composition thereof and the concomitant drug or a pharmaceutical composition thereof, which have been separately produced, by the same administration route in a staggered manner, (4) simultaneous administration of two kinds of preparations of the TLR4 signal transduction inhibitory substance of the present invention or a pharmaceutical composition thereof and the concomitant drug or a pharmaceutical composition thereof, which have been separately produced, by different administration routes, (5) administration of two kinds of preparations of the TLR4 signal transduction inhibitory substance of the present invention or a pharmaceutical composition thereof and the concomitant drug or a pharmaceutical composition thereof, which have been separately produced, by different administration routes in a staggered manner (for example, administration in the order of the TLR4 signal transduction inhibitory substance of the present invention or a pharmaceutical composition thereof and the concomitant drug or a pharmaceutical composition thereof, or in the reverse order) and the like.

The combination ratio of the TLR4 signal transduction inhibitory substance of the present invention and a concomitant drug in the combination drug of the present invention can be appropriately determined depending on the administration object, administration route, disease and the like.

For example, the content of a cycloalkene compound or compound A in the combination drug of the present invention varies depending on the form of the preparation. It is generally about 0.01-99.8 wt %, preferably about 0.1-50 wt %, more preferably about 0.5-20 wt %, based on the preparation in total.

The content of the concomitant drug in the combination drug of the present invention varies depending on the form of the preparation. It is generally about 0.01-99.8 wt %, preferably about 0.1-50 wt %, more preferably about 0.5-20 wt %, based on the preparation in total.

The content of the additive, such as a carrier, in the combination drug of the present invention varies depending on the form of the preparation. It is generally about 1-99.98 wt %, preferably about 10-90 wt %, based on the preparation in total.

When the TLR4 signal transduction inhibitory substance of the present invention is prepared into separate pharmaceutical preparations, similar contents can be employed.

When the TLR4 signal transduction inhibitory substance of the present invention is administered to a human, it can be safely administered orally or parenterally as it is or in a mixture with an appropriate pharmacologically acceptable carrier, excipient and diluent, in a pharmaceutical composition such as an oral formulation (e.g., powder, granule, tablet, capsule etc.), a parenteral formulation (e.g., injection, external formulation (e.g., nasal formulation, percutaneous formulation etc.) and suppository (e.g., rectal suppository and vaginal suppository etc.).

Any of these formulations may be produced by any method known per se which is employed ordinarily for producing a pharmaceutical formulation. The combination ratio of the TLR4 signal transduction inhibitory substance of the present invention to be incorporated into a formulation may vary depending on the dosage forms, and is preferably about 10 to 95% by weight in an oral formulation described above and about 0.001 to about 95% by weight in a parenteral formulation described above.

For example, the TLR4 signal transduction inhibitory substance of the present invention can be prepared into an aqueous injection together with a solubilizer (e.g., β-cyclodextrins etc.), a dispersant (e.g., Tween 80 (manufactured by ATLASPOWDER USA), HCO 60 (manufactured by NIKKO CHEMICALS), carboxymethylcellulose, sodium arginate etc.), a preservative (e.g., methyl paraben, propyl paraben, benzyl alcohol chlorobutanol etc.), an isotonic agent (e.g., sodium chloride, glycerine, sorbitol, glucose etc.) and the like, or into an oil-based injection by dissolving, suspending or emulsifying using a vegetable oil (e.g., olive oil, sesame oil, peanut oil, cottonseed oil, corn oil etc.) and propylene glycol and the like.

An oral formulation can be produced by a method known per se by, for example, compressing the TLR4 signal transduction inhibitory substance of the present invention together with an excipient (e.g., lactose, sucrose, starch etc.), a disintegrant (e.g., starch, calcium carbonate etc.), a binder (e.g., starch, gum arabic, carboxymethyl cellulose, polyvinyl pyrrolidone, hydroxypropyl cellulose etc.), a lubricant (e.g., talc, magnesium stearate, polyethylene glycol 6000 etc.), and the like, followed by, where necessary, a coating process known per se for the purpose of masking a taste, forming an enteric coat, or achieving a sustained release. For such coating may be used, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (manufactured by ROHM, Germany, a copolymer of methacrylic acid and acrylic acid), a dye (e.g., titanium oxide, colcothar etc.) and the like.

The TLR4 signal transduction inhibitory substance of the present invention can also be employed as an external formulation in the form of a solid or semi-solid or liquid.

For example, a solid external formulation may be the TLR4 signal transduction inhibitory substance of the present invention as it is or may be produced by mixing the substance with an excipient (e.g., glycol, mannitol, starch, crystalline cellulose etc.), a thickening agent (e.g., natural gums, cellulose derivatives, acrylic acid polymers etc.) and the like and processing the mixture into a powder composition. A semi-solid external formulation may be produced by a conventional method and preferably used in the form of an aqueous or oil-based gel or ointment. A liquid external formulation may be produced in the form of an oil-based or aqueous suspension by a method employed for producing an injection formulation or an analogous method.

The solid, semi-solid or liquid external formulation may be supplemented also with a pH modifier (e.g., carbonic acid, phosphoric acid, citric acid, hydrochloric acid, sodium hydroxide etc.), an antiseptic (e.g., p-hydroxybenzoate esters, chlorobutanol, benzalkonium chloride etc.) and the like, as appropriate. Typically, vaseline or lanolin is used as a formulation base, per 1 g of which about 0.1 to 100 mg of the TLR4 signal transduction inhibitory substance of the present invention is contained to form an ointment.

The TLR4 signal transduction inhibitory substance of the present invention may be also formulated as an oil or aqueous, solid or semi-solid or liquid suppository by a method known per se. As an oil base, for example, a high fatty acid glyceride (e.g., cocoa butter, WITEPSOL (manufactured by DYNAMIT NOBEL, Germany) etc.), a middle fatty acid (e.g., MYGLYOL (manufactured by DYNAMIT NOBEL, Germany) etc.), a vegetable oil (e.g., sesame oil, soybean oil, cottonseed oil etc.) and the like are used as appropriate. An aqueous base may be, for example, polyethylene glycol or propylene glycol, and an aqueous gel base may be, for example, a natural gum, a cellulose derivative, a vinyl polymer, an acrylic polymer and the like.

While the dose of the TLR4 signal transduction inhibitory substance of the present invention varies depending on the patient's age, body weight and condition, the dosage form, the mode and the period of the treatment, the dose of the TLR4 signal transduction inhibitory substance of the present invention may be, for example, generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg, as the amount of the TLR4 signal transduction inhibitory substance of the present invention, per day for the treatment of sepsis (adult weighing about 60 kg), and said daily dose is given orally or parenterally all at once or in several portions a day. It is a matter of course that a lower daily dose may be sufficient or an excessive dose may be required since the dose may vary depending on various factors as discussed above.

While the dose of the combination drug of the present invention varies depending on the kind of the compound, the patient's age, body weight and condition, the dosage form, the mode and the period of the treatment, the dose of the combination drug may be, for example, generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg, as the amount of the TLR4 signal transduction inhibitory substance of the present invention and the concomitant drug, per day for the treatment of sepsis (adult weighing about 60 kg), said daily dose being given intravenously all at once or in several portions during a day. It is a matter of course that a lower daily dose may be sufficient or an excessive dose may be required since the dose may vary depending on various factors as discussed above.

The concomitant drug may be contained in any amount as long as a side effect does not pose a problem. While the daily dose of the concomitant drug may vary depending on the disease state, the age, sex, body weight and difference in sensitivity of the administration object, timing and interval of administration, characteristics, dispensing and kind of the pharmaceutical preparation, the kind of active ingredient and the like and is not particularly limited, the amount of the drug is generally about 0.001-2000 mg, preferably about 0.01-500 mg, more preferably about 0.1-100 mg, per 1 kg body weight of mammal by oral administration, which is generally administered all at once or in 2 to 4 portions during a day.

When the combination drug of the present invention is administered, the TLR4 signal transduction inhibitory substance of the present invention and a concomitant drug may be administered at the same time, or a concomitant drug may be administered first, and then the TLR4 signal transduction inhibitory substance of the present invention may be administered. Alternatively, the TLR4 signal transduction inhibitory substance of the present invention may be administered first, and then the concomitant drug may be administered. For time staggered administration, the time difference varies depending on the active ingredient to be administered, dosage form and administration route. For example, when a concomitant drug is to be administered first, the TLR4 signal transduction inhibitory substance of the present invention is administered within 1 min-3 days, preferably 10 min-1 day, more preferably 15 min-1 hour, after the administration of the concomitant drug. When the TLR4 signal transduction inhibitory substance of the present invention is to be administered first, the concomitant drug is administered within 1 min-1 day, preferably 10 min-6 hours, more preferably 15 min-1 hour, after the administration of the concomitant drug.

EXAMPLES

The present invention is explained in detail in the following by referring to Examples, which are not to be construed as limitative.

Example 1

DNAs wherein the 3'- and 5'-ends of various cDNAs have a restriction enzyme site were amplified by a conventional method using polymerase chain reaction (PCR). The primer was as follows.
TIRAP:

```
                                         (SEQ ID NO: 5)
  5'-GCGCGGATCCATGGCATCATCGACCTCCCT-3'

(SEQ ID NO: 6)
  5'-GCGCGCGGCCGCTCAAAGTAGATCAGATA-3'
```

TLR2 intracellular TIR domain:

```
                                         (SEQ ID NO: 7)
  5'-GGATCCTATGATGCATTTGTTTCTTACAGT-3'

(SEQ ID NO: 8)
  5'-AAGCGGCCGCCTAGGACTTTATCGCAGCTCTCAG-3'
```

TLR4 intracellular TIR domain:

```
                                         (SEQ ID NO: 9)
  5'-GGATCCTATGATGCCTTTGTTATCTACTCA-3'

(SEQ ID NO: 10)
  5'-AAGCGGCCGCTCAGATAGATGTTGCTTCCTGCCA-3'
```

Using the above-mentioned primer DNA and TAKARA Ex Taq and after first standing at 95° C. for 2 min in a thermal cycler, PCR was performed 30 cycles with 95° C. for 30 sec, at 55° C. for 30 sec and at 72° C. for 1 min as one cycle. Lastly, an elongation reaction was performed at 72° C. for 10 min. The amplified DNA fragment was cloned using a TA Cloning Kit (Invitrogen). The obtained plasmid vector was treated with a restriction enzyme and electrophoresed on agarose gel. The band was cleaved out using a Sephaglas B and Prep Kit (Amersham) and purified. This was inserted as an insert into vector plasmid pGEX-4T-1 (Amersham) using DNA ligation kit Ver.2 (TAKARA).

Escherichia coli was transformed with the completed plasmid, and cultured in LB medium containing ampicillin (10 mL) at 37° C. for 18 hr. Culture medium (2.4 mL) was inoculated to LB medium containing ampicillin (130 mL), and subjected to shaking culture. When $OD_{600}$ became amount 0.9, isopropyl-β-D-thiogalactopyranoside (1 mol/L) was added (130 μL), and the mixture was cultivated at 30° C. for 4 hr. After cultivation, the cells were collected and 10 mL of Lysis Buffer (10 mmol/L Tris pH 7.5, 150 nmol/L NaCl, 0.5% triton-X-100, 1 mmolp/L PMSF) was added. The cells were disrupted by ultrasonication and centrifuged. To the obtained supernatant was added Glutathione Sepharose 4B (Amersham, 300 μL), and the mixture was gently shaken at 4° C. for 60 min. After the reaction, GST fusion protein-bound beads were washed with TBS (Tris buffered saline, 50 mM Tris-HCl pH7.5, 150 mM NaCl) added with 0.1% Triton X-100.

The completed GST fusion protein-bound beads and $^3$H-compound A (synthesized by Amersham) were reacted at 4° C. overnight. After the reaction, the beads were washed with 0.1% Triton X-100 added TBS, a sample buffer for 5% 2-mercaptoethanol (ME)-containing sodium dodecyl sulfate (SDS)-polyacrylamide gel electrophoresis (PAGE) was added, and the mixture was heated at 100° C. for 5-10 min. The mixture was centrifuged, the supernatant was separated as a labeled protein sample, and the protein was separated by SDS-PAGE. The gel containing the separated protein was immobilized with 40% methanol-10% acetic acid solution, stained with CBB (FIG. 1A), placed on a filter and dried by a gel dryer. The dry gel and imaging plate TR2040 (FUJI-FILM Corporation) were closely adhered to each other to allow photosensitization and the amount of $^3$H bound to the protein was measured (autoradiography) by BAS-2500 (FUJIFILM Corporation). $^3$H-compound A was selectively bound to GST-TLR4 intracellular TIR domain fusion protein, and was not bound to other GST fusion protein and GST (FIG. 1B).

Example 2 cDNA encoding TLR4 was obtained by a conventional method using PCR, and incorporated into expression vector pEFBos. Each point mutant was produced using QuikChange II Site-directed Mutagenesis Kit (manufactured by Stratagene). A mismatch corresponding to a mutation was introduced into both ends of a primer according to the manual of the kit. The produced primers are as follows (mutant introduction sites are underlined). Thereafter, a mutant was produced according to the manual and a competent cell was transformed therewith. Single colonies were picked up, a plasmid was prepared according to a conventional method and DNA sequence was confirmed to give a plasmid containing each mutant TLR4.

1CA:
```
                                         (SEQ ID NO: 11)
  5'-TGATGCTTCTTGCTGGCGCCATAAAGTATGGTAGAG-3'
                                         (SEQ ID NO: 12)
  5'-CTCTACCATACTTTATGGCGCCAGCAAGAAGCATCA-3'
```

2CA:
```
                                         (SEQ ID NO: 13)
  5'-CCTCCATTTCAGCTCGCCCTTCACTACAGAGA-3'
                                         (SEQ ID NO: 14)
  5'-TCTCTGTAGTGAAGGGCGAGCTGAAATGGAGG-3'
```

3CA:
```
                                         (SEQ ID NO: 15)
  5'-ATCCAGAGCCGCTGGGCTATCTTTGAATATGA-3'
                                         (SEQ ID NO: 16)
  5'-TCATATTCAAAGATAGCCCAGCGGCTCTGGAT-3'
```

-continued

4CA:
(SEQ ID NO: 17)
5'-ACAGTGGGTACAGGAGCCAATTGGCAGGAAGC-3'
(SEQ ID NO: 18)
5'-GCTTCCTGCCAATTGGCTCCTGTACCCACTGT-3'

PH:
(SEQ ID NO: 19)
5'-TACAGAGACTTTATTCACGGTGTGGCCATTGC-3'
(SEQ ID NO: 20)
5'-GCAATGGCCACACCGTGAATAAAGTCTCTGTA-3'

1KR:
(SEQ ID NO: 21)
5'-CAGTTCTGGTCTATAGGTTCTATTTTCACCTG-3'
(SEQ ID NO: 22)
5'-CAGGTGAAAATAGAACCTATAGACCAGAACTG-3'

2KR:
(SEQ ID NO: 23)
5'-TGCTGGCTGCATAAGGTATGGTAGAGGTG-3'
(SEQ ID NO: 24)
5'-CACCTCTACCATACCTTATGCAGCCAGCA-3'

3KR:
(SEQ ID NO: 25)
5'-GGAATGAGCTAGTAAGGAATTTAGAAGAAGG-3'
(SEQ ID NO: 26)
5'-CCTTCTTCTAAATTCCTTACTAGCTCATTCC-3'

4KR:
(SEQ ID NO: 27)
5'-CATGAAGGTTTCCATAGAAGCCGAAAGGTGATT-3'
(SEQ ID NO: 28)
5'-AATCACCTTTCGGCTTCTATGGAAACCTTCATG-3'

5KR:
(SEQ ID NO: 29)
5'-CCATAAAAGCCGAAGGGTGATTGTTGTGG-3'
(SEQ ID NO: 30)
5'-CCACAACAATCACCCTTCGGCTTTTATGG-3'

6KR:
(SEQ ID NO: 31)
5'-CATTGTCCTGCAGAGGGTGGAGAAGACC-3'
(SEQ ID NO: 32)
5'-GGTCTTCTCCACCCTCTGCAGGACAATG-3'

7KR:
(SEQ ID NO: 33)
5'-CAGAAGGTGGAGAGGACCCTGCTCAGGC-3'
(SEQ ID NO: 34)
5'-GCCTGAGCAGGGTCCTCTCCACCTTCTG-3'

8KR:
(SEQ ID NO: 35)
5'-GAGACGACTCAGAAGAGCCCTGCTGGATG-3'
(SEQ ID NO: 36)
5'-CATCCAGCAGGGCTCTTCTGAGTCGTCTC-3'

9KR:
(SEQ ID NO: 37)
5'-CCTGCTGGATGGTAGATCATGGAATCCAGA-3'
(SEQ ID NO: 38)
5'-TCTGGATTCCATGATCTACCATCCAGCAGG-3'

*Escherichia coli* was transformed with the produced plasmids, about 500-700 µg thereof was each purified using EndoFree (R) Plasmid Maxi Kit (Quiagen). African green monkey aderenogenic cell COS-7 was washed twice with OPTI-MEM (Invitrogen), and the medium was changed from DMEM (Invitrogen) containing 10% FCS, 100 µg/mL streptomycin and 100 U/mL penicillin to OPTI-MEM 5 mL/dish. A plasmid encoding FLAG-TLR4WT or each mutant was transfected into COS-7 cells using a PLUS reagent (Invitrogen) or a LipofectAMINE reagent (Invitrogen) according to a conventional method, and the cells were cultured for 3 hr at 37° C., 5% $CO_2$. DMEM containing 20% FCS was added at 6.5 mL/dish, and the cells were further cultured for 2 days.

The medium was changed to DMEM (5 mL) containing 1% FCS, $^3$H-compound A (synthesized by Amersham) was added to a final concentration of 100 nmol/L, and the cells were cultured for 6 hr at 37° C., 5% $CO_2$. After culture, the cells were washed with PBS (5 mL) once and a lysis buffer (10 mmol/L Tris pH 7.5, 150 mmol/L NaCl, 0.1% Nonidet P-40, 0.05% 3-((3-cholamidopropyl dimethylammonio)-1-propanesulfonate (CHAPS), 30 mmol/L NaF, 1 mmol/L $Na_3VO_4$ and Protease inhibitor cocktail (Sigma)) was added to 1 mL/dish. The petri dish containing the lysis buffer was placed on ice for 15 min to solubilize the cells. The cells were centrifuged (12000 rpm, 4° C., 10 min) to remove insoluble fraction and the supernatant was recovered and used as a total cell lysate.

The obtained total cell lysate was used to perform immunoprecipitation by an anti-FLAG antibody according to a conventional method. Anti-FLAG M2 antibody (Sigma, 30 µg) was added, and the mixture was reacted for 3 hr while gently shaking at 4° C. Protein A Sepharose beads (50 µL) were added, and the mixture was reacted overnight while gently shaking at 4° C. The next day, the beads were washed three times with the lysis buffer, a sample buffer for SDS-PAGE, containing 5% 2-ME, was added, and the mixture was heated at 100° C. for 10 min. The mixture was centrifuged, and the supernatant free of the beads was used as an immunoprecipitate.

Figure 2:
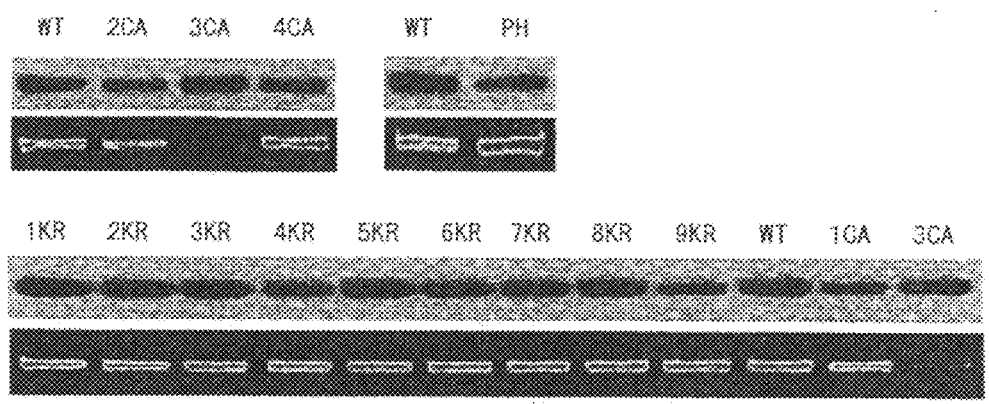
FIG. 2 shows the binding ability of $^3$H-labeled compound A with wild-type TLR4 and various mutant TLR4s. The upper panel shows immunoblot images of the TLR protein expression levels, and the lower panel shows autoradiographs showing binding of compound A. WT: wild-type TLR4; 1CA: TLR4$^{C666A}$ (indicating the 666th C is substituted by A, hereinafter the same); 2CA: TLR$^{C706A}$; 3CA: TLR4$^{C747A}$; 4CA: TLR$^{C831A}$; PH: TLR$^{P714H}$; 1KR: TLR$^{K653R}$; 2KR: TLR$^{K666R}$; 3KR: TLR$^{K694R}$; 4KR: TLR$^{K729R}$; 5KR: TLR$^{K732R}$; 6KR: TLR$^{K773R}$; 7KR: TLR$^{K776}$; 8KR: TLR$^{K813R}$; 9KR: TLR$^{K819R}$

The immunoprecipitated was applied to SDS-PAGE to separate the protein, and the gel after migration was immersed in a blotting buffer for 15 min to remove SDS. The gel was closely adhered to a polyvinylidene difluoride (PVDF) membrane, and the protein in the gel was transferred to the PVDF membrane by a wet transfer apparatus. The PVDF membrane carrying the protein was blocked in Tris-HCl buffer containing 3% (W/V) nonfat milk (50 mmol/L Tris, 138 mmol/L NaCl, 2.7 mmol/L KCl, pH 8.0), primary antibody (anti-FLAG M2 10 µg/mL) and reacted for 2 hr with Tris-HCl buffer containing 3% milk. After washing, the primary antibody was reacted for 1 hr with the secondary antibody (HRP-anti mouse IgG) and the protein bound to the HRP-labeled antibody was treated with an ECL reagent. The luminescence of the band was photographed on an X ray film, Kodak Biomax-MS, and the protein expression level was confirmed (FIG. 2; the upper panel). The photographed PVDF membrane was washed with PBS-T, photosensitized on imaging plate TR-2040 for 7 days, and the amount of $^3$H bound to the expressed protein was measured using BAS-2500 (FUJIFILM Corporation). The binding amount of $^3$H-compound A remarkably decreased only when 747th cysteine of TLR4 was mutated to alanine (FIG. 2; the lower panel). It was clarified that compound A was selectively bound to the 747th cysteine.

Example 3

Human embryonic kidney-derived HEK293 was suspended in DMEM containing 10% FCS, plated in a 96 well plate at $2 \times 10^4$ cells/well and cultured overnight at 37° C., 5% $CO_2$. The medium was changed to OPTI-MEM (Invitrogen, 50 µL/well) immediately before transfection. A plasmid encoding FLAG-TLR4WT or a mutant thereof (0CA-3CA, PH, 1KR-9KR) was added to 0.5 ng/well, and transfection was performed using a PLUS reagent (Invitrogen) or a LipofectAMINE reagent (Invitrogen) according to a conventional method. The cells were cultured at 37° C., 5% $CO_2$ for 3 hr. After culture, DMEM containing 20% FCS was added to 100 µL/well, and the cells were further cultured overnight to give forced expression cells. As common DNAs, pNiFty (plasmid for NF-κB activation measurement, 15 ng/well), phRL-TK (internal standard plasmid, 15 ng/well), MD-2 plasmid (10 ng/well) and CD14 plasmid (10 ng/well) were transfected together with wild-type TLR4 and each mutant.

The next day of the transfection, the medium of the forced expression cells was changed to DMEM containing 1% FCS, compound A (ethyl (6R)-6-[N-(2-chloro-4-fluorophenyl)sulfamoyl]-1-cyclohexene-1-carboxylate), compound B (d-ethyl 6-[N-(2,4-difluorophenyl)sulfamoyl]-1-cyclohexene-1-carboxylate), compound C (ethyl 6-[N-(2-bromo-4-fluorophenyl)sulfamoyl]-1-cyclohexene-1-carboxylate), compound D (d-ethyl 6-[(2-chloro-4-fluorobenzyl)sulfonyl]-1-cyclohexene-1-carboxylate) were added to the final concentration of 0, 30, 100, 300 nmol/L and the cells were cultured for 2 hr at 37° C., 5% $CO_2$. LPS was added to 100 ng/mL, and the cells were further cultured for 4 hr. After culture, the luminescence of luciferase was measured using Dual-Glo™ Luciferase Assay System (Promega). For the measurement, the luminescence of firefly luciferase (derived from FL, NF-κB activation) and renilla luciferase (RL, internal standard) was measured, and CPS (counts per second) of FL was amended by CPS of RL to give FL/RL ratio. The results are shown in FIG. 3.

The signal suppressing action by compound A, compound B, compound C and compound D disappeared only when the 747th cysteine of TLR4 was mutated to alanine. Hence, it was clarified that compound A, compound B, compound C and compound D selectively bind to the 747th cysteine to suppress the signal.

INDUSTRIAL APPLICABILITY

Using the screening method of the present invention, a substance that binds to an intracellular region of TLR4 and inhibits signal transduction of TLR4 can be selected. The obtained substance is useful as a drug for the prophylaxis or treatment of cardiac diseases, autoimmune diseases, inflammatory diseases, central nervous system diseases, infectious diseases, sepsis, severe sepsis or septic shock.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

This application is based on patent application No. 2006-095936 filed in Japan, and the contents disclosed therein are hereby entirely incorporated by reference. In addition, the contents disclosed in any publication cited herein, including patents and patent applications, are hereby incorporated in their entireties by reference, to the extent that they have been disclosed herein.

The invention claimed is:

1. A method of screening for a drug for the treatment of inflammatory disease, sepsis, severe sepsis or septic shock, comprising the following steps (a) to (d):

(a) preparing a cell that expresses TLR4 (toll-like receptor 4) and contains a gene under regulation of a promoter containing an NF-κB (nuclear factor κB) or IRF3 (interferon regulatory factor 3) binding sequence (sample 1), and a cell that expresses a mutant TLR4 comprising SEQ ID NO: 2, except that the 747$^{th}$ amino acid residue of SEQ ID NO: 2 has been mutated to a different amino acid than found at the 747$^{th}$ amino acid residue of SEQ ID NO: 2, and contains a gene under regulation of a promoter containing an NF-κB or IRF3 binding sequence (sample 2), (b) culturing sample 1 and sample 2 each in the presence of a test compound, (c) measuring the expression of the gene in sample 1 and sample 2 after culture, and (d) selecting, when the level of gene expression in sample 1 decreases by not less than about 20% than that in sample 2, the test compound as a substance that binds to TLR4 via the intracellular region of TLR4 to inhibit signal transduction from TLR4.

2. The method of claim 1, wherein the gene is a reporter gene.

* * * * *